US008962023B2

(12) United States Patent
Labrecque et al.

(10) Patent No.: US 8,962,023 B2
(45) Date of Patent: *Feb. 24, 2015

(54) UV CURED GEL AND METHOD OF MAKING

(75) Inventors: Roger Labrecque, Londonderry, NH (US); Philip McNamara, Concord, NH (US); Joseph Ferraro, Londonderry, NH (US); Lisa Rogers, Londonderry, NH (US); Paul Martakos, Pelham, NH (US); Theodore Karwoski, Hollis, NH (US); Steve A. Herweck, Nashua, NH (US); Keith Faucher, Nashua, NH (US); Thomas M. Swanick, Hillsborough, NH (US)

(73) Assignee: Atrium Medical Corporation, Hudson, NH (US)

( * ) Notice: Subject to any disclaimer, the term of this patent is extended or adjusted under 35 U.S.C. 154(b) by 1014 days.

This patent is subject to a terminal disclaimer.

(21) Appl. No.: 11/236,943

(22) Filed: Sep. 28, 2005

(65) Prior Publication Data

US 2006/0067975 A1    Mar. 30, 2006

Related U.S. Application Data

(60) Provisional application No. 60/613,808, filed on Sep. 28, 2004.

(51) Int. Cl.

| A61K 9/00 | (2006.01) |
|---|---|
| A61L 27/54 | (2006.01) |
| A61F 13/02 | (2006.01) |
| A61K 9/06 | (2006.01) |
| A61K 31/225 | (2006.01) |
| A61K 31/355 | (2006.01) |
| A61K 47/12 | (2006.01) |
| A61K 47/14 | (2006.01) |
| A61L 2/07 | (2006.01) |
| A61L 2/08 | (2006.01) |
| A61L 2/20 | (2006.01) |
| A61L 27/36 | (2006.01) |
| A61L 27/52 | (2006.01) |
| A61L 31/00 | (2006.01) |
| A61L 31/10 | (2006.01) |
| A61L 31/14 | (2006.01) |
| A61F 2/06 | (2013.01) |
| B05D 3/06 | (2006.01) |

(52) U.S. Cl.
CPC ............ *A61L 27/54* (2013.01); *A61F 13/02* (2013.01); *A61F 13/023* (2013.01); *A61K 9/0024* (2013.01); *A61K 9/06* (2013.01); *A61K 31/225* (2013.01); *A61K 31/355* (2013.01); *A61K 47/12* (2013.01); *A61K 47/14* (2013.01); *A61L 2/07* (2013.01); *A61L 2/081* (2013.01); *A61L 2/087* (2013.01); *A61L 2/206* (2013.01); *A61L 2/208* (2013.01); *A61L 27/36* (2013.01); *A61L 27/52* (2013.01); *A61L 31/005* (2013.01);
*A61L 31/10* (2013.01); *A61L 31/145* (2013.01); *A61F 2/06* (2013.01); *A61F 2250/0067* (2013.01); *A61L 2202/24* (2013.01); *A61L 2300/22* (2013.01); *A61L 2300/252* (2013.01); *A61L 2300/404* (2013.01); *A61L 2300/41* (2013.01); *A61L 2300/414* (2013.01); *A61L 2300/42* (2013.01); *A61L 2300/602* (2013.01); *B05D 3/067* (2013.01)
USPC ........... 424/484; 424/422; 424/423; 424/425; 424/486; 514/785

(58) Field of Classification Search
None
See application file for complete search history.

(56) References Cited

U.S. PATENT DOCUMENTS

| 3,556,294 | A | | 1/1971 | Walck et al. |
|---|---|---|---|---|
| 3,803,109 | A | * | 4/1974 | Nemoto et al. ............... 522/40 |
| 3,967,728 | A | | 7/1976 | Gordon et al. |
| 4,308,120 | A | | 12/1981 | Pennewiss et al. |
| 4,323,547 | A | | 4/1982 | Knust et al. |
| 4,664,114 | A | | 5/1987 | Ghodstain |
| 4,813,210 | A | | 3/1989 | Masuda et al. |

(Continued)

FOREIGN PATENT DOCUMENTS

| EP | 0471566 | 2/1992 |
|---|---|---|
| EP | 0610731 | 8/1994 |

(Continued)

OTHER PUBLICATIONS

Websters Dictionary Online, Accessed on Feb. 13, 2009, entry for "polymer" p. 1 of 1.*
"polymerization" Merriam-Webster Online Dictionary, retrieved from <www.merriam-webster.com> on Dec. 13, 2009; Merriam-Webster's Inc. 2009; pp. 1.*
Shahidi, Fereidoon ed.; "Bailey's Industrial Oil and Fat Products" 2005; John Wiley and Sons; vol. 5, Edible Oil and Fat Products: Processing Technologies, pp. 1-15.*

(Continued)

*Primary Examiner* — David J Blanchard
*Assistant Examiner* — Ivan Greene
(74) *Attorney, Agent, or Firm* — Morse, Barnes-Brown & Pendleton, P.C.; Sean D. Detweiler, Esq.

(57) ABSTRACT

A method of UV curing and corresponding resulting non-polymeric cross-linked gel are provided. The cross-linked gel can be combined with a medical device structure. The cross-linked gel can provide anti-adhesion characteristics, in addition to improved healing and anti-inflammatory response. The cross-linked gel is generally formed of a naturally occurring oil, or an oil composition formed in part of a naturally occurring oil, that is at least partially cured forming a cross-linked gel derived from at least one fatty acid compound. In addition, the oil composition can include a therapeutic agent component, such as a drug or other bioactive agent. The curing method can vary the application of UV light in both intensity and duration to achieve a desired amount of cross-linking forming the gel.

15 Claims, 11 Drawing Sheets

(56) References Cited

U.S. PATENT DOCUMENTS

| | | | |
|---|---|---|---|
| 4,814,329 A | 3/1989 | Harsanyi et al. |
| 4,847,301 A | 7/1989 | Murray |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,938,763 A | 7/1990 | Dunn et al. |
| 4,941,308 A | 7/1990 | Grabenkort et al. |
| 4,968,302 A | 11/1990 | Schluter et al. |
| 5,017,229 A | 5/1991 | Burns et al. |
| 5,147,374 A | 9/1992 | Fernandez |
| 5,151,272 A | 9/1992 | Engstrom et al. |
| 5,171,148 A | 12/1992 | Wasserman et al. |
| 5,179,174 A | 1/1993 | Elton |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,403,283 A | 4/1995 | Luther |
| 5,447,940 A | 9/1995 | Harvey et al. |
| 5,464,650 A | 11/1995 | Berg et al. |
| 5,480,653 A | 1/1996 | Aguadisch et al. |
| 5,509,899 A | 4/1996 | Fan et al. |
| 5,579,149 A | 11/1996 | Moret et al. |
| 5,580,923 A | 12/1996 | Yeung et al. |
| 5,591,230 A | 1/1997 | Horn et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,736,152 A | 4/1998 | Dunn |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A * | 1/2000 | Exsted et al. ............. 428/305.5 |
| 6,015,844 A | 1/2000 | Harvey et al. |
| 6,028,164 A | 2/2000 | Loomis |
| 6,040,330 A | 3/2000 | Hausheer et al. |
| 6,056,970 A | 5/2000 | Greenawalt et al. |
| 6,077,698 A | 6/2000 | Swan et al. |
| 6,083,950 A | 7/2000 | Anand et al. |
| 6,090,809 A | 7/2000 | Anand et al. |
| 6,117,911 A | 9/2000 | Grainger et al. |
| 6,120,789 A | 9/2000 | Dunn |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 * | 1/2002 | Soudant et al. ............. 424/753 |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,491,938 B2 | 12/2002 | Kunz |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 | 4/2003 | Sadozai et al. |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,730,064 B2 | 5/2004 | Ragheb et al. |
| 6,753,071 B1 | 6/2004 | Pacetti |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,101,381 B2 | 9/2006 | Ford et al. |
| 7,152,611 B2 | 12/2006 | Brown et al. |
| 7,415,811 B2 | 8/2008 | Gottlieb et al. |
| 8,124,127 B2 * | 2/2012 | Faucher et al. ............. 424/484 |
| 8,263,102 B2 * | 9/2012 | Labrecque et al. ......... 424/423 |
| 8,367,099 B2 * | 2/2013 | Herweck et al. ........... 424/447 |
| 8,501,229 B2 * | 8/2013 | Faucher et al. ............. 424/484 |
| 8,722,077 B2 | 5/2014 | Labrecque et al. |
| 2001/0025034 A1 * | 9/2001 | Arbiser ....................... 514/114 |
| 2001/0025196 A1 | 9/2001 | Chinn et al. |
| 2001/0051595 A1 | 12/2001 | Lyons et al. |
| 2002/0002154 A1 | 1/2002 | Guivarc'h et al. |
| 2002/0007209 A1 | 1/2002 | Scheerder et al. |
| 2002/0012741 A1 | 1/2002 | Heinz et al. |
| 2002/0032414 A1 | 3/2002 | Ragheb et al. |
| 2002/0055701 A1 | 5/2002 | Fischell et al. |
| 2002/0098278 A1 | 7/2002 | Bates et al. |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0142089 A1 | 10/2002 | Koike et al. |
| 2002/0193829 A1 | 12/2002 | Kennedy et al. |
| 2003/0003125 A1 | 1/2003 | Nathan et al. |

(56) References Cited

U.S. PATENT DOCUMENTS

| | | |
|---|---|---|
| 2003/0004564 A1 | 1/2003 | Elkins et al. |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0108588 A1* | 6/2003 | Chen et al. .......... 424/423 |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2004/0006296 A1 | 1/2004 | Fischell et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0071756 A1 | 4/2004 | Fischell et al. |
| 2004/0073284 A1 | 4/2004 | Bates et al. |
| 2004/0117007 A1 | 6/2004 | Whitbourne et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0230176 A1 | 11/2004 | Shanahan et al. |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0158361 A1 | 7/2005 | Dhondt et al. |
| 2005/0159809 A1 | 7/2005 | Hezi-Yamit et al. |
| 2005/0182485 A1 | 8/2005 | Falotico et al. |
| 2005/0187376 A1 | 8/2005 | Pacetti |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067976 A1 | 3/2006 | Ferraro et al. |
| 2006/0067977 A1 | 3/2006 | Labrecque et al. |
| 2006/0068674 A1 | 3/2006 | Dixit et al. |
| 2006/0083768 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0212411 A1 | 9/2007 | Fawzy et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0038307 A1 | 2/2008 | Hoffmann |
| 2008/0044481 A1 | 2/2008 | Harel |
| 2008/0086216 A1 | 4/2008 | Wilson et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2008/0286440 A1 | 11/2008 | Scheer |
| 2009/0011116 A1 | 1/2009 | Herweck et al. |
| 2009/0047414 A1 | 2/2009 | Corbeil et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2012/0016038 A1 | 1/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 A1 | 1/2003 |
| EP | 1364628 | 11/2003 |
| EP | 1520795 | 4/2005 |
| EP | 1557183 | 7/2005 |
| EP | 2083875 | 8/2009 |
| EP | 1402906 | 6/2011 |
| KR | 20080025986 | 3/2008 |
| WO | WO 86/00912 | 7/1984 |
| WO | WO 90/01969 | 3/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | WO 98/54275 | 12/1998 |
| WO | WO 99/25336 | 5/1999 |
| WO | WO-00/40278 A1 | 7/2000 |
| WO | WO-00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO-02/100455 | 12/2002 |
| WO | WO-03/000308 A1 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 A1 * | 5/2003 |
| WO | WO 03/041756 | 5/2003 |
| WO | WO 03/039612 A1 * | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |

(56) References Cited

FOREIGN PATENT DOCUMENTS

WO    WO 2008/057328    5/2008
WO    WO 2012/009707    1/2012

OTHER PUBLICATIONS

Sweetman, Sean C; "Martindale: The complete drug reference," 33$^{rd}$ ed., 2002, Pharmaceutical Press; pp. 1-90.*
Drugs.com "Drug Index A to Z", retrieved from <www.drugs.com> on Apr. 1, 2013; pp. 1-4.*
Garner, Brian A.; "A Dictionary of Modern Legal Usage," Second ed. 1987; pp. 389-390; and 713-717.*
Pearlman, Daniel D & Paula R.; "Guide to Rapid Revision," 3$^{rd}$ ed. 1982; Bobbs-Merril Educational Publishing; pp. 25-27.*
Canter, Sheryl; "Chemistry of Cast Iron Seasoning: A Science-Based How-To", retrieved from <sherylcanter.com> on Apr. 5, 2013; pp. 1-5, as provided.*
O'Neil, Maryadelle J. et al.; "The Merck Index—An Encyclopedia of Chemicals, Drugs, and Biologicals, 14$^{th}$ ed." 2006; entries for "Calcium Carbonate," "Cyclosporins," "Prussian Blue," and "Rapamycin", pp. 1-12, as provided.*
Nagao et al.; "Conjugated Fatty Acids in Food and Their Health Benefits," 2005, The Society for Biotechnology, Japan; Journal of Bioscience and Bioengineering, vol. 100, No. 2, pp. 152-157.*
Goodnight et al.; "Polyunsaturated Fatty Acids, Hyperlipidemia, and Thrombosis," 1982, American Heart Association; Journal of the American Heart Association, vol. 2, No. 2, pp. 87-113.*
Drugs.com "Drug Index A to Z", retrieved from on Apr. 1, 2013; pp. 1-4.*
Sweetman, Sean C; "Martindale: The complete drug reference," 33rd ed., 2002, Pharmaceutical Press; pp. 1-90.*
Andres, Vicente & Castro, Claudia; "Antiproliferative Strategies for the Treatment of Vascular Proliferative Disease," 2003, Bentham Science Pubs.; Current Vascular Pharamacology, vol. 1, No. 1, pp. 85-98.*
International Search Report for Application No. PCT/US05/34941, dated May 4, 2006.
A paper entitled, "Evaluation of the Biocompatibility and Drug Delivery Capabilities of Biological Oil Based Stent Coatings," by Li, Shengqiao of the Katholieke Universiteit Leuven.
Ahuja et al., "Prevention of Postoperative Intraperitoneal Adhesions—An Experimental Study in Rats", Journal of Indian Pediatric Surgery, 7:15-20 (2002).
Jonasson, Lena et al., "Cyclosporon A inhibits smooth muscle proliferation in the vascular response to injury," Proc. Natl. Acad. Sci. USA, vol. 85: 2303-2306 (1988).
Ogunniyi, D.S., "Castor oil: A vital industrial raw material," Biosource Technology, vol. 97: 1086-1091 (2006).
Redman, L.V. et al., "The drying rate of raw paint oils—a comparison," The Journal of Industrial and Engineering Chemistry, vol. 5: 630-636 (1913).
Jorge, N., "Grasas y Aceites", 48(1): 17-24, (1997).
International Search Report for PCT/US2011/44292, dated Dec. 6, 2011.
International Search Report for International Application PCT/US05/034941, dated May 4, 2006.
Supplementary European Search Report for EP12004057, dated Apr. 10, 2013.
Advisory Action for U.S. Appl. 12/581,582 (listed on SB-08 as U.S. Publication No. 20100183697), dated Nov. 14, 2012.
Notice of Allowance for U.S. Appl. No. 11/525,390 (listed on SB-08 as U.S. Publication No. US-2007-0071798), dated Nov. 20, 2012.
Non-Final Office Action for U.S. Appl. No. 13/404,487 (listed on SB-08 as US 20120213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. Publication No. US-2008-0118550, dated Feb. 19, 2013.
Non-Final Office Action for U.S. Appl. No. 13/682,991 (listed on SB-08 as U.S. Publication No. US- 2013-0074452), dated Mar. 18, 2013.
Notice of Allowance for U.S. Appl. No. 13/404,487 (listed on SB-08 as U.S. Publication No. US- 2012-0213839), dated Apr. 2, 2013.
Non-Final Office Action for U.S. Appl. No. 11/236,943 (listed on SB-08 as U.S. Publication No. US- 2006-0067975), dated Apr. 22, 2013.
Final Office Action for U.S. Appl. No. 13/184,512 (listed on SB-08 as U.S. Publication No. U.S. 2012-0016038), date Jun. 25, 2013.
Non-Final Office Action for U.S. Appl. No. 11/237,264 (listed on SB-08 as U.S. Publication No. US-2006-0067983), dated Jul. 3, 2013.
Non-Final Office Action for U.S. Appl. No. 13/593,656 (listed on SB-08 as U.S. Publication No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
International Search Report for International Application PCT/US2013/044653, dated Sep. 4, 2013.
Mallegol, "Long-Term Behavior of Oil-Based Varnishes and Paints Photo-and Thermooxidation of Cured Linseed Oil", Journal of the American Oil Chemists' Society, 77:257-263 (2000).
Non-Final Office Action for U.S. Appl. No. 11/237,420 (listed on SB-08 as U.S. Publication No. US-2006-0078586), dated Nov. 12, 2013.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
Notice of Allowance for U.S. Appl. No. 13/593,656 (listed on SB-08 as U.S. Publication 2012-03115219), dated Jan. 24, 2014.
Final Office Action for U.S. Appl. No. 11/237,264 (listed on SB-08 as U.S. Publication No. US-2006-0067983), dated Dec. 17, 2013.
Autosuture, "ParietexTM Composite OS Series Mesh," retrieved online at http://www.autosuture.com/AutoSuture/pagebuilder.aspx?topicID=135734&breadcrumbs=135601:0 (2007).
Binder et al., "Chromatographic Analysis of Seed Oils. Fatty Acid Composition of Castor Oil," The Journal of the American Oil Chemists' Society, vol. 39:513-517 (1962).
Camurus, "In our endeavors to create the unique, we start with the best. Your product.".
CECW-EE, "Ch. 4: Coating Types and Characteristics," Engineering and Design—Painting: New Construction and Maintenance, pp. 4-1 to 4-24 (1995).
De Scheerder, Ivan K., et al. "Biocompatibility of polymer-coated oversized metallic stents implanted in normal porcine coronary arteries," Atherosclerosis, vol. 114:105-114. (1995).
Drummond, Calum J., et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei, et al, "Physiological Transport Forces Govern Drug Distribution for Stent-Based Delivery," Circulation, vol. 104:600-605 (2001).
Mallegol, et al., "Drier Influence on the Curing of Linseed Oil," Progress in Organic Coatings 39:107-113 (2000).
Morse, Richard "Molecular Distillation of Polymerized Drying Oils," Industrial and Engineering Chemisry 33:1039-1043 (1941).
Oberhoff, Martin, et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).

(56) References Cited

OTHER PUBLICATIONS

Salu, Koen J., et al, "Addition of cytochalasin D to a biocompatible oil stent coating inhibits intimal hyperplasia in a porcine coronary model," Coronary Artery Disease, vol. 14(8):545-555 (2003).
Scheller, Bruno, et al, "Addition of Paclitaxel to Contrast Media Prevents Restenosis After Coronary Stent Implantation," Journal of the American College of Cardiology, vol. 42(8):1415-1420 (2003).
Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).
Wikipedia, "Sirolimus," pp. 1-13, available online at http://en.wikipedia.org/wiki/Sirolimus, date accessed May 11, 2011.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
Timir-Balizsy et al., "Chemical Principals of Textile Conservation," Oxford: Elsevier Science Ltd., 1998:117-119.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
Supplementary European Search Report for Application No. EP 08877338.7, dated Aug. 16, 2012.
Supplementary European Search Report for Application No. EP09819594.4, dated Aug. 14, 2012.
Non-final Office Action for U.S. Appl. No. 11/236,908 (listed on SB/08 as US 2006/0067974), mailed Mar. 25, 2006.
Final Office Action for U.S. Appl. No. 11/236,908 (listed on SB/08 as US 2006/0067974), mailed May 17, 2011.
Non-final Office Action for U.S. Appl. No. 11/236,908 (listed on SB/08 as US 2006/0067974), mailed Aug. 24, 2009.
Non-final Office Action for U.S. Appl. No. 11/236,977 (listed on SB/08 as US 2006/0088596), mailed Aug. 3, 2009.
Final Office Action for U.S. Appl. No. 11/237,263 (listed on SB/08 as US 2006/0110457), mailed Jul. 7, 2010.
Non-final Office Action for U.S. Appl. No. 11/237,263 (listed on SB/08 as US 2006/0110457), mailed Oct. 7, 2009.
Final Office Action for U.S. Appl. No. 11/237,264 (listed on SB/08 as US 2006/0067983), mailed Jun. 2, 2010.
Non-final Office Action for U.S. Appl. No. 11/237,264 (listed on SB/08 as US 2006/0067983), mailed Oct. 5, 2009.
Final Office Action for U.S. Appl. No. 11/701,799 (listed on SB/08 as US 2008/0109017), mailed Nov. 23, 2010.
Non-final Office Action for U.S. Appl. No. 11/237,420 (listed on SB/08 as US 2006/0078586), mailed Mar. 5, 2009.
Final Office Action for U.S. Appl. No. 11/237,420 (listed on SB/08 as US 2006/0078586), mailed Nov. 4, 2009.
Non-final Office Action for U.S. Appl. No. 11/237,420 (listed on SB/08 as US 2006/0078586), mailed Dec. 6, 2010.
Non-final Office Action for U.S. Appl. No. 11/238,532 (listed on SB/08 as US 2006/0067976), mailed Mar. 30, 2009.
Final Office Action for U.S. Appl. No. 11/238,532 (listed on SB/08 as US 2006/0067976), mailed Sep. 9, 2009.
Final Office Action for U.S. Appl. No. 11/238,554 (listed on SB/08 as US 2006/0121081), mailed May 12, 2010.
Non-final Office Action for U.S. Appl. No. 11/238,554 (listed on SB/08 as US 2006/0121081), mailed Oct. 9, 2009.
Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 11/980,155 (listed on SB/08 as US 2008/0113001), mailed Mar. 24, 2011.
Non-final Office Action for U.S. Appl. No. 12/075,223 (listed on SB/08 as US 2008/0206305), mailed Dec. 8, 2010.

(56) References Cited

OTHER PUBLICATIONS

Non-final Office Action for U.S. Appl. No. 12/325,546 (listed on SB/08 as US 2009/0181937), mailed Feb. 25, 2010.
Final Office Action for U.S. Appl. No. 12/325,546 (listed on SB/08 as US 2009/0181937), mailed Aug. 31, 2010.
Non-final Office Action for U.S. Appl. No. 12/364,763 (listed on SB/08 as US 2009/0208552), mailed Dec. 11, 2009.
Final Office Action for U.S. Appl. No. 12/364,763 (listed on SB/08 as US 2009/0208552), mailed Sep. 21, 2010.
Interview summary for U.S. Appl. No. 11/236,908 (listed on SB/08 as US 2006/0067974), mailed May 5, 2009.
Interview summary for U.S. Appl. No. 11/236,908 (listed on SB/08 as US 2006/0067974), mailed Dec. 2, 2010.
Interview summary for U.S. Appl. No. 11/237,420 (listed on SB/08 as US 2006/0078586), mailed May 5, 2009.
Interview summary for U.S. Appl. No. 11/582,135 (listed on SB/08 as US 2007/0202149), mailed Dec. 7, 2010.
Interview summary for U.S. Appl. No. 12/325,546 (listed on SB/08 as US 2009/0181937), mailed Dec. 2, 2010.
Interview summary for U.S. Appl. No. 12/364,763 (listed on SB/08 as US 2009/0208552), mailed Dec. 2, 2010.
Final Office Action for U.S. Appl. No. 11/237,420 (listed on SB/08 as US 2006/0078586), mailed Jul. 13, 2011.
Final Office Action for U.S. Appl. No. 11/978,840 (listed on SB/08 as US 2008/0118550), mailed Jun. 22, 2011.
Final Office Action for U.S. Appl. No. 12/075,223 (listed on SB/08 as US 2008/0206305), mailed Aug. 11, 2011.
Non-final Office Action for U.S. Appl. No. 11/525,390 (listed on SB/08 as US 2007/0071798), mailed Jul. 11, 2011.
Non-Final Office Action for U.S. Appl. No. 11/701,799 (listed on SB/08 as US 2008/0109017), mailed Aug. 17, 2011.
Non-Final Office Action for U.S. Appl. No. 11/582,135 (listed on SB/08 as US-2007-0202149), mailed Oct. 14, 2011.
Final Office Action for U.S. Appl. No. 11/980,155 (listed on SB/08 as US-2008-0113001), mailed Oct. 21, 2011.
Non-Final Office Action for U.S. Appl. No. 11/236,908 (listed on SB/08 as US-2006-0067974), mailed Dec. 2, 2011.
Non-Final Office Action for U.S Appl. No. 12/182,261 (listed on SB/08 as US 2009-0047414), mailed Dec. 21, 2011.
Non-Final Office Action for U.S. Appl. No. 12/401,243 (listed on SB/08 as US 2010-0233232), mailed Jan. 5, 2012.
Notice of Allowance for U.S. Appl. No. 11/582,135 (listed on SB/08 as US 2007-0202149), mailed Jan. 9, 2012.
Non-Final Office Action for U.S. Appl. No. 12/182,165 (listed on SB/08 as US 2009-0011116), mailed Jan. 5, 2012.
Final Office Action for U.S. Appl. No. 11/701,799 (listed on SB/08 as US 2008/0109017), mailed Feb. 13, 2012.
Non-Final Office Action for U.S. Appl. No. 12/581,582 (listed on SB/08 as US 20100183697), mailed Mar. 14, 2012.
Final Office Action for U.S. Appl. No. 12/182,165 (listed on SB/08 as US 2009-0011116), mailed Apr. 6, 2012.
Final Office Action for U.S. Appl. No. 12/182,261 (listed on SB-08 as US 2009/0047414), mailed Apr. 30, 2012.
Notice of Allowance for U.S. Appl. No. 11/236,908 (listed on SB/08 as US-2006-0067974), mailed May 11, 2012.
Final Office Action for U.S. Appl. No. 12/401,243 (listed on SB/08 as US-2010-0233232), mailed Jun. 11, 2012.
Notice of Allowance for U.S. Appl. No. 12/182,261 (listed on SB/08 as US US-20090047414), mailed Jul. 23, 2012.
Advisory Action for U.S. Appl. No. 12/401,243 (listed on SB/08 as US 2010-0233232), mailed Aug. 27, 2012.
Final Office Action for U.S. Appl. No. 12/581,582 (listed on SB-08 as US 2010/0183697), mailed Aug. 29, 2012.
Notice of Allowance for U.S. Appl. No. 11/525390 (listed on SB/08 as US-2007/0071798), mailed Oct. 4, 2012.
Notice of Allowance for U.S. Appl. No. 11/237,264 (listed on SB-08 as U.S. Publication No. US-2006-0067983), dated Mar. 27, 2014.
Notice of Allowance for U.S. Appl. No. 11/237,263 (listed on SB-08 as U.S. Publication No. US-US-2006-0110457), dated Mar. 27, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum,*, 47; 2157-2162 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Non Final Office Action for U.S. Appl. No. 12/581,582 (listed on SB-08 as U.S. Publication 2010-0183697), dated May 29, 2014.
Non-Final Office Action for U.S. Appl. No. 13/943,489, dated Jul. 1, 2014.
Final Office Action for U.S. Appl. No. 11/980,155, dated Jul. 21, 2014.
Final Office Action for U.S. Appl. No. 11/237,420, dated Jul. 22, 2014.
Non-Final Office Action for U.S. Appl. No. 11/701,799, dated Jul. 22, 2014.
Final Office Action for U.S. Appl. No. 12/075,223, dated Jul. 22, 2014.
Supplementary European Search Report for Application No. EP 10825447, dated Mar. 31, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.
Non Final Office Action for U.S. Appl. No. 12/401,243 (listed on SB/08 as US 20100233232), mailed May 8, 2014.
Non-Final Office Action for U.S. Appl. No. 13/843,068, dated Sep. 29, 2014.
Non-Final Office Action for U.S. Appl. No. 13/184,512, dated Oct. 10, 2014.
Non-Final Office Action for U.S. Appl. No. 12/075,223, dated Oct. 29, 2014.
Non-Final Office Action for U.S. Appl. No. 11/980,155, dated Nov. 7, 2014.
Notice of Allowance for U.S. Appl. No. 12/364,763, dated Dec. 5, 2014.
Notice of Allowance for U.S. Appl. No. 12/325,546, dated Dec. 8, 2014.

* cited by examiner

US 8,962,023 B2

UV CURED GEL AND METHOD OF MAKING

RELATED APPLICATIONS

This application claims priority to, and the benefit of, U.S. Provisional Application No. 60/613,808, filed Sep. 28, 2004, for all subject matter common to both applications. The disclosure of said provisional application is hereby incorporated by reference in its entirety. This application also relates to co-pending U.S. patent application Ser. No. 11/237,420, filed concurrently with this application on Sep. 28, 2005.

FIELD OF THE INVENTION

The present invention relates to coatings for medical devices, or films, which are cured, and more particularly to a method of UV curing a coating or stand alone film formed at least in part of a non-polymeric cross-linked gel cured a desired amount, and the resulting structure provided by the curing process.

BACKGROUND OF THE INVENTION

Coatings and drugs, agents, or compounds are utilized in combination with a number of medical devices, and in particular with implantable medical devices such as stents, stent-grafts, surgical meshes, vascular grafts, and the like. Other devices such as vena cava filters and anastomosis devices may also be used with coatings having drugs, agents, or compounds therein. In addition, surgical medical film is often used in surgical settings, such as in patients undergoing abdominal or pelvic laparotomy as an adjunct intended to reduce the incidence, extent, and severity of postoperative adhesions between different tissues and organs and implantable medical devices such as soft tissue support membranes and mesh.

In general, such coatings and films are manufactured utilizing polymeric based materials. The coatings and films are formed using a number of different manufacturing techniques. However, there has been little progress in the manufacture of coatings or films utilizing non-polymeric based materials in a manner that can form the desired coating or film, with desired degradation properties, while maintaining some of the anti-inflammatory, non-inflammatory, and wound healing properties of some of the non-polymeric substances available.

More specifically, oils are occasionally briefly mentioned as being a potential carrier component for the delivery of a therapeutic from a medical device. However, there has been little development with regard to the determination of how to accomplish the provision of a non-polymeric coating containing a therapeutic, or even a non-polymeric coating maintaining its original anti-inflammatory, non-inflammatory, or wound healing properties. Some of these anti-inflammatory, non-inflammatory, and wound healing characteristics can be found in oils containing fatty acids, especially omega-3 fatty acids, such as fish oil. However, there is little known relating to methods for configuring non-polymeric coatings to carry therapeutic agents in a manner that results in a predefined, desired, rate of degradation to provide for the controlled release of the therapeutic agent or the controlled degradation of the coating.

SUMMARY OF THE INVENTION

What is desired is a method of making a non-polymeric biological oil based coating on a medical device or in the form of a stand alone film, which exhibits properties such as anti-adhesion, anti-inflammation, non-inflammation, and enhanced wound healing, to the local tissue that can also be further enhanced with the application of one or more therapeutic agents or medications for absorption into the tissue that is in contact with the coating or film. The method of making directly influences the resulting coating or film and corresponding rate of degradation of the coating or film following implantation, and thus the controlled release of any therapeutic agents contained within. The method of curing also influences the level of inherent anti-inflammation, non-inflammation, and wound healing properties of certain biological oils that is able to be maintained after curing. The present invention is directed toward further solutions to address this need.

Curing with respect to the present invention generally refers to thickening, hardening, or drying of a material brought about by heat, UV, or chemical means.

In accordance with one embodiment of the present invention, a method of curing to form a gel includes providing a non-polymeric substance to be cured. An amount of cross-linking desired within the substance as a result of curing is determined. UV light is applied at a selected intensity for a selected time period based on the determination of amount of cross-linking desired to achieve the desired amount of cross-linking within the substance to form the gel.

In accordance with aspects of the present invention, the substance to be cured can be an oil or oil composition. The substance to be cured can contain fatty acids. The substance to be cured can include at least one therapeutic agent. The agent can be any one or more of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the step of determining includes selecting the amount of cross-linking based on a desired rate of degradation of the gel following implantation. The application of UV light/heat occurs at a relatively greater intensity if more cross-linking is desired and at a relatively lesser intensity if a lesser amount of cross-linking is desired. The application of UV light occurs for a relatively greater duration of time if more cross-linking is desired and at a relatively lesser duration of time if a lesser amount of cross-linking is desired. A relatively faster rate of degradation provides for a relatively faster release of therapeutic agent contained within the gel, while a relatively slower rate of degradation provides for a relatively slower and more controlled release of therapeutic agent contained within the gel.

In accordance with further aspects of the present invention, the non-polymeric substance to be cured at least partially includes at least partially cured oil to reduce the amount of time required to achieve the desired amount of cross-linking.

In accordance with further aspects of the present invention, the cross-linked gel is configured to provide controlled release of a therapeutic agent component. The cross-linked gel is bio-absorbable. The cross-linked gel maintains at least one property, such as anti-inflammatory properties, non-inflammatory properties, and wound healing properties.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with further aspects of the present invention, the method can include sterilizing the cross-linked gel with a method of sterilization, such as ethylene oxide, gamma radiation, e-beam, steam, gas plasma, or vaporized hydrogen peroxide (VHP).

In accordance with one embodiment of the present invention, a UV cured non-polymeric gel includes a collection of non-polymeric cross-links resulting from application of UV light/heat at a selected intensity for a selected duration to achieve a desired amount of cross-linking to form the non-polymeric gel.

In accordance with aspects of the present invention, the gel can be derived from an oil or oil composition. The gel can be derived from a substance comprising fatty acids. The gel can include at least one therapeutic agent. The agent can be any one or more of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the gel is configured to maintain a desired rate of degradation of the gel following implantation. The gel formed with application of UV light at a relatively higher intensity if more cross-linking is desired and at a relatively lower intensity if a lesser amount of cross-linking is desired. The gel is formed with application of UV light/heat for a relatively greater duration of time if more cross-linking is desired and at a relatively lesser duration of time if a lesser amount of cross-linking is desired.

In accordance with further aspects of the present invention, the gel is formed from at least partially pre-cured oil to reduce the amount of time required to achieve the desired amount of cross-linking. The cross-linked gel is configured to provide controlled release of a therapeutic agent component. The cross-linked gel is bio-absorbable. The cross-linked gel maintains at least one property, such as anti-inflammatory properties, non-inflammatory properties, or wound healing properties.

In accordance with further aspects of the present invention, the gel has been sterilized with a method of sterilization including ethylene oxide, gamma radiation, e-beam, steam, gas plasma, or vaporized hydrogen peroxide (VHP).

In accordance with further aspects of the present invention, the gel is configured as a coating on a medical device or as a stand-alone film. Furthermore, the non-polymeric substance used to form the gel can be pre-treated to increase viscosity prior to curing.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION

Figure 1:
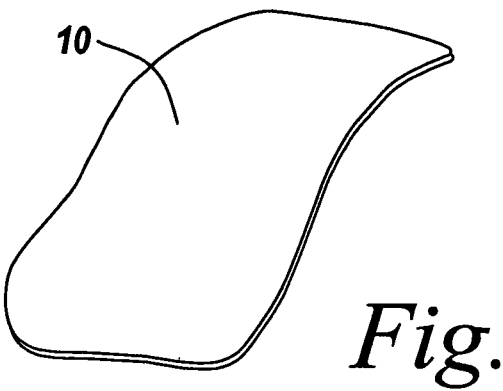
FIG. 1 is a diagrammatic illustration of a cross-linked gel realized as a stand alone film, according to one embodiment of the present invention.

An illustrative embodiment of the present invention relates to the provision of a coating or film that is a cured cross-linked gel and can exhibit anti-inflammatory properties, non-inflammatory properties, anti-adhesion properties, and/or wound healing properties, and corresponding method of making. The cross-linked gel can be its own medical device (i.e., a stand alone film), or the cross-linked gel can be combined with another medical device to provide the desired characteristics, in addition to potentially delivering therapeutic agents. The cross-linked gel is generally formed of a naturally occurring oil, or an oil composition formed in part of a naturally occurring oil having fatty acids. In addition, the oil composition can include a therapeutic agent component, such as a drug or other bioactive agent. The cross-linked gel is implantable in a patient, or applied on the skin surface of the patient, for short term or long term applications, and can include controlled release of the therapeutic agent. As implemented herein, the cross-linked gel is a non-polymeric cross-linked gel derived at least in part from a fatty acid compound.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances, such as polymers, can cause inflammatory response due to either the parent substance or those substances formed during breakdown, and they may or may not be absorbed by tissues. Bio-absorbable substances break down into substances or components that do not cause an inflammatory response and can be consumed by the cells forming the body tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-cross-linked semi-solid. Hydrogenation can reduce or eliminate omega-3 fatty acids, and any therapeutic effects (both anti-inflammatory and wound healing) they offer.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that received a polymer-based implant must also follow a course of long term systemic anti-platelet therapy, on a permanent basis, to offset the thrombogenic properties of the non-absorbable polymer. A significant percentage of patients that receive such implants are required to undergo additional medical procedures, such as surgeries (whether related follow-up surgery or non-related surgery) and are required to stop their anti-platelet therapy. This can lead to a thrombotic event, such as stroke, which can lead to death. Use of the inventive coating described herein can negate the necessity of anti-platelet therapy, and the corresponding related risks described, because there is no thrombogenic polymer reaction to the coating. Other polymer implant patients must follow a course of systemic anti-inflammatory therapy, to offset the inflammatory properties of the non-absorbable polymer. Typical anti-inflammatory agents are immunosupressants and systemic delivery of anti-inflammatory agents can sometimes lead to additional medical complications, such as infection or sepsis, which can lead to long term hospitalization or death. Use of the non-polymeric cross-linked gel of the inventive coating described herein may also negate the necessity of anti-inflammatory therapy, and the corresponding related risks described, because there is no inflammatory reaction to an oil barrier formed in accordance with the present invention.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some application of UV light to the omega-3 fatty acids to cure the oil can lessen the total therapeutic effectiveness of the omega-3 fatty acids, but not eliminate the therapeutic effectiveness. One characteristic that can remain after certain curing by UV methods is the non-inflammatory response of the tissue when exposed to the cured omega-3 fatty acid material. As such, an oil containing omega-3 fatty acids can be exposed to UV light for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other barrier or coating materials.

It should be noted that as utilized herein to describe the present invention, the terms vitamin E, vitamin E compound, and alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

FIGS. 1 through 9, wherein like parts are designated by like reference numerals throughout, illustrate an example embodiment of a non-polymeric biological oil cross-linked gel cured to form a coating or film using ultraviolet (UV) light according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a non-polymeric cross-linked gel 10 in accordance with one embodiment of the present invention. The cross-linked gel 10 is flexible, to the extent that it can be placed in a flat, curved, or rolled, configuration within a patient. The cross-linked gel 10 is implantable, for both short term and long term applications. Depending on the particular formulation of the cross-linked gel 10, the cross-linked gel 10 will be present after implantation for a period of hours to days, or possibly months.

The cross-linked gel 10 is formed of an oil component. The oil component can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an anti-adhesion agent. In addition, the fish oil maintains anti-inflammatory or non-inflammatory properties as well. The present invention is not limited to formation of the film or gel with fish oil as the naturally occurring oil. However, the following description makes reference to the use of fish oil as one example embodiment. Other naturally occurring oils can be utilized in accordance with the present invention as described herein.

It should be noted that as utilized herein, the term fish oil fatty acid includes but is not limited to omega-3 fatty acid, fish oil fatty acid, free fatty acid, esters of fish oil, triglycerides, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked gel, creating the cross-linked gel 10.

It should further be noted that FIG. 1 represents merely one embodiment of the cross-linked gel 10. The cross-linked gel 10 serves as a biological oil barrier and, depending on degree of cure, can also serve as a physical barrier, as depicted. The biological oil barrier is represented by the application of the fatty acid based oil, such as fish oil, onto a medical device. Such a configuration provides a biological oil cross-linked gel that provides a non-inflammatory or anti-inflammatory barrier coating. Using a number of different methods as described below, the biological oil can be cured to create a non-polymeric cross-linked gel. In the instance of the medical device taking the form of a surgical mesh, the biological oil can be cured to the extent that the cells or pores of the mesh are substantially or completely bridged by the cured biological oil creating a physical barrier. With such a configuration there remains some biological oil that is not cured but is interdispersed within the cured oil and maintains the biological oil cross-linked gel as well. Thus, substantial curing creates both a biological oil cross-linked gel and a physical barrier. The physical barrier provides anti-adhesive properties of the barrier as discussed herein. Additional embodiments can include the provision of the substantially cured oil forming the biological oil cross-linked gel with physical layer, and then a subsequent application of the biological oil as a top coat. This creates a more substantial biological oil cross-linked gel supported by the combination biological oil cross-linked gel and physical cross-linked gel.

One aspect of the cross-linked gel 10 mentioned above is that it has anti-adhesion characteristics or properties. By anti-adhesion, what is meant is a characteristic whereby the incidence, extent, and severity of postoperative adhesions, or lacerations or other tissue injuries, between different tissues and organs is reduced. The anti-adhesion characteristic results from the materials used to form the cross-linked gel 10.

More specifically, the cross-linked gel 10 provides a lubricious or anti-adhesive surface against tissue. The cross-linked gel 10 itself, in its substantially cured configuration, can provide a physical anti-adhesion barrier between two sections of tissue, or the cross-linked gel 10 can form an anti-adhesion surface on a medical device, such as the mesh 40. The use of the naturally occurring oil, such as fish oil, provides extra lubrication to the surface of the medical device, which helps to reduce injury. With less injury, there is less of an inflammatory response, and less healing required. The biological oil barrier created by the fatty acid oil derived cross-linked gel likewise provides anti-inflammatory properties and non-inflammatory properties, thus reducing the occurrence of inflammatory response and also adhesions due to inflammation. The oily surface of the cross-linked gel 10 provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the cross-linked gel 10 can vary. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature or UV light exposure conditions, more cross-links form transitioning the gel from a relatively liquid gel to a relatively solid-like, but still flexible, gel structure.

Another aspect of the present invention is that the cross-linked gel 10 is formed of the bio-absorbable material, such as naturally occurring fish oil, in accordance with the example embodiment described herein. The bio-absorbable properties of the naturally occurring oil enable the cross-linked gel 10 to be absorbed by the cells of the body tissue (i.e., bio-absorbable). In example embodiments of the present invention, the bio-absorbable cross-linked gel contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the cross-linked gel of the present invention described herein. Accordingly, fatty acids and alpha-tocopherol can be combined in differing amounts and ratios to contribute to a cross-linked gel in a manner that provides control over the cellular uptake characteristics of the cross-linked gel and any therapeutic agents mixed therein.

For example, the amount of alpha-tocopherol can be varied in the cross-linked gel. Alpha-tocopherol (vitamin E compound) is known to slow autoxidation in fish oil by reducing hydroperoxide formation, which results in a decrease in the amount of cross-linking in cured fish oil. It has been shown that even with fewer cross-links, the addition of varying amounts of alpha-tocopherol can be used to increase the time in which the cross-linked gel degrades compared to a cross-linked gel of fish oil alone. The addition of alpha-tocopherol to the oil or oil composition prior to forming the cross-linked gel can result in fewer cross-links when compared with the oil without alpha-tocopherol. Although there are fewer cross-links, the degradation period is extended with the alpha-tocopherol added. In addition alpha-tocopherol can be used to increase solubility of drugs in the fish oil forming the cross-linked gel. Thus, varying the amount of alpha-tocopherol present in the cross-linked gel can impact the resulting formation. Alpha-tocopherol can actually protect the therapeutic drug during curing, which increases the resulting drug load in the cross-linked gel after curing. Furthermore, with certain therapeutic drugs, the increase of alpha-tocopherol in the cross-linked gel serves to slow and extend drug release due to the increased solubility of the drug in the alpha-tocopherol component of the cross-linked gel. This reflects the cellular uptake inhibitor functionality of alpha-tocopherol, in that the uptake of the drug is slowed and extended over time.

It should further be emphasized that the bio-absorbable nature of the cross-linked gel results in the cross-linked gel 10 being completely absorbed over time by the cells of the body tissue. There are no substances in the cross-linked gel, or break down products of the cross-linked gel, that induce an inflammatory response. The cross-linked gel 10 is generally composed of, or derived from, omega-3 fatty acids bound to triglycerides, potentially also including a mixture of free fatty acids and vitamin E compounds (alpha-tocopherol). The triglycerides are broken down by lipases (enzymes) which result in free fatty acids that can than be transported across cell membranes. Subsequently, fatty acid metabolism by the cell occurs to metabolize any substances originating with the cross-linked gel. The bio-absorbable nature of the cross-linked gel of the present invention results in the cross-linked gel being absorbed over time, leaving only an underlying delivery or other medical device structure that is biocompatible. There is no foreign body inflammatory response to the bio-absorbable cross-linked gel.

Although the present invention is bio-absorbable to the extent that the cross-linked gel 10 experiences the uptake into or through body tissues, in the specific embodiment described herein formed using naturally occurring oils, the exemplar oils are also lipid based oils. The lipid content of the oils provides a highly bio-absorbable cross-linked gel 10. More specifically, there is a phospholipids layer in each cell of the body tissue. The fish oil, and equivalent oils, contain lipids as well. There is a lipophilic action that results where the lipids are attracted by each other in an effort to escape the aqueous environment surrounding the lipids.

A further aspect of the cross-linked gel 10 is that the specific type of oil can be varied, and can contain elements beneficial to healing. The cross-linked gel also provides a natural scaffold for cellular growth and remodeling with clinical applications in general surgery, spinal repair, orthopedic surgeries, tendon and ligament repairs, gynecological and pelvic surgeries, and nerve repair applications. The addition of therapeutic agents to the cross-linked gels used in these applications can be utilized for additional beneficial effects, such as pain relief or infection minimization. In addition, non-surgical applications include external wound care, such as a treatment for burns or skin ulcers, without therapeutics as a clean, non-permeable, non-adhesive, anti-inflammatory, non-inflammatory dressing, or with added therapeutics for additional beneficial effects. The cross-linked gel may also be used as a transdermal drug delivery patch.

The process of wound healing involves tissue repair in response to injury and it encompasses many different biologic processes, including epithelial growth and differentiation, fibrous tissue production and function, angiogenesis, and inflammation. The inventive cross-linked gel has been shown in an animal model not to produce an inflammatory response, but still provide excellent cellular overgrowth with little to no fibrous capsule formation. Accordingly, the cross-linked gel provides an excellent material suitable for wound healing applications.

Another aspect of the cross-linked gel 10 mentioned above is that the cross-linked gel 10 can contain therapeutic agents for delivery to the body tissue. Therapeutic agents have been delivered to a targeted location in a human utilizing a number of different methods in the past. For example, agents may be delivered nasally, transdermally, intravenously, orally, or via other conventional methods. Delivery may vary by release rate (i.e., quick release or slow release). Delivery may also vary as to how the drug is administered. Specifically, a drug may be administered locally to a targeted area, or administered systemically.

As utilized herein, the phrase "therapeutic agent(s)" refers to a number of different drugs or agents available, as well as future agents that may be beneficial for use with the cross-linked gel of the present invention. Therapeutic agents can be added to the cross-linked gel 10, and/or the medical device in combination with the cross-linked gel 10 as discussed herein. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, antiseptics, analgesics, prodrugs, and any additional desired therapeutic agents such as those listed in Table 1 below.

TABLE 1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyano-acrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |

TABLE 1-continued

| CLASS | EXAMPLES |
|---|---|
| Local Tissue perfusion | Alcohol, H2O, saline, fish oils, vegetable oils, liposomes |
| Nitric oxide Donor Derivatives | NCX 4016 - nitric oxide dono derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma - 1b, Interluekin - 10 |
| Immunosuppressive/ Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose tha are combined with dimethylamino-propyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200, 985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term ranging generally within a matter of seconds or minutes to a few days or weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer. Accordingly, the effect of the therapeutic agent is substantially local at the surface of the tissue making contact with the medical device having the coating. In some instances the effect of the therapeutic agent is further localized to the specific locations of, for example, stent struts pressed against the tissue location being treated. These prior approaches can create the potential for a localized toxic effect.

The cross-linked gel 10 of the present invention, however, makes use of the natural oils to form a non-polymeric natural oil based therapeutic agent delivery platform, if desired. Furthermore, the cross-linked gel 10 can be formed in a manner that creates the potential for controlled long term release of a therapeutic agent, while still maintaining the benefits of the natural oil component of the cross-linked gel 10.

More specifically, it is known that oil that is oxygenated becomes a waxy solid. Attempts have been made to convert the polyunsaturated oils into a wax or solid to allow the oil to adhere to a device for a longer period of time. One such approach applies the oil to the medical device and allows the oil to dry.

With the present invention, and in the field of soft tissue applications, and in part because of the lipophilic mechanism enabled by the bio-absorbable lipid based cross-linked gel 10 of the present invention, the uptake of the therapeutic agent is facilitated by the delivery of the therapeutic agent to the cell membrane by the bio-absorbable cross-linked gel 10. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

In addition, when the oil provided to form the cross-linked gel 10 is a naturally occurring oil containing the omega-3 fatty acids (including DHA and EPA), the process for forming the cross-linked gel 10 can be tailored to avoid causing detrimental effects to the beneficial properties of the omega-3 fatty acids, or at least effects too detrimental to have any lasting effect. As described herein, certain properties of the fatty acids may lose their effectiveness, however other desired properties are maintained. If there is no concern for maintaining the beneficial effects, the curing and other steps leading to the formation of the cross-linked gel 10 can include steps that may reduce some of the beneficial properties of the omega-3 fatty acids, as understood by one of ordinary skill in the art.

Example embodiments illustrating the formation and different configurations of the cross-linked gel 10 are provided herein.

The cross-linked gel 10 of the present invention serves as a non-polymeric biological oil based cross-linked gel and can also serve as a physical cross-linked gel if sufficiently cured. In accordance with the example embodiments described herein, the cross-linked gel is formed of a non-polymeric cross-linked gel derived from fatty acid compounds. The fatty acid compounds include omega-3 fatty acids when the oil utilized to form the cross-linked gel is fish oil or an analog or derivative thereof. As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the cross-linked gel after the (C=C) bonds have substantially isomerized into the trans configuration. The (C=C) bonds can also form C—C cross-linking bridges in the glyceride hydrocarbon chains using a Diels-Alder Reaction. In addition to solidifying the cross-linked gel through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

The non-polymeric cross-linked gel derived from fatty acid compounds, such as those of fish oil, includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the gel. The cross-linked gel degrades into fatty acid, short and long chain alcohol, and glyceride molecules, which are all non-inflammatory and likewise consumable by cells in the soft tissue to which the cross-linked gel is applied. Thus, the cross-linked gel is bio-absorbable.

UV initiated curing (photo-oxygenation) in accordance with the present invention involves the interaction between a double bond and singlet oxygen produced from ordinary triplet oxygen by light and typically in the presence of a sensitizer such as chlorophyll or methylene blue and results in the formation of hydroperoxides. The chemical reaction is described in the following graphic.

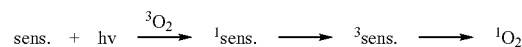

Since the above described reaction is not a radical chain process, it possess no induction period and is typically unaffected by antioxidants commonly used to inhibit autoxidation. However, this reaction can be inhibited by single oxygen quenchers such as carotene. This reaction is limited to C=C carbon atoms and results in a conversion from cis to trans C=C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments of the present invention.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C=C sites as shown for linolenate in the below graphic.

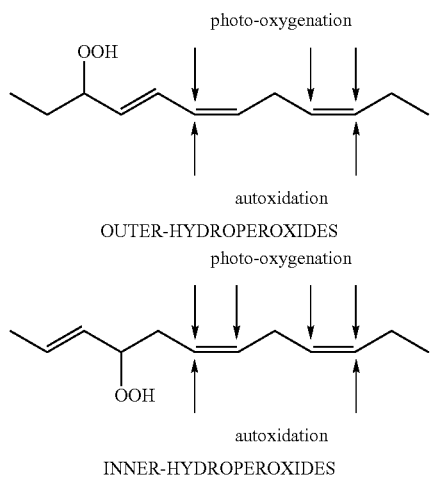

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed where autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Figure 2A:
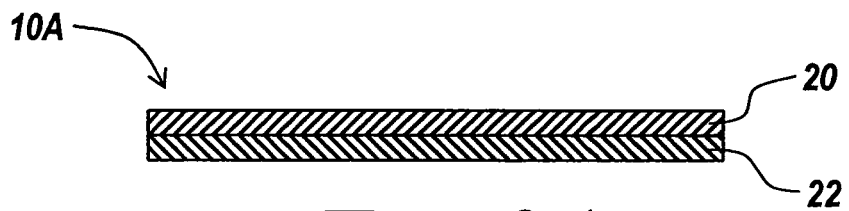
FIGS. 2A, 2B, and 2C are cross-sectional views of the cross-linked gel in accordance with one aspect of the present invention.
Figure 2B:
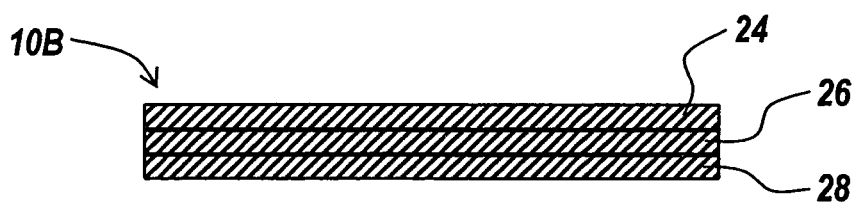
Figure 2C:
Figure 3A:
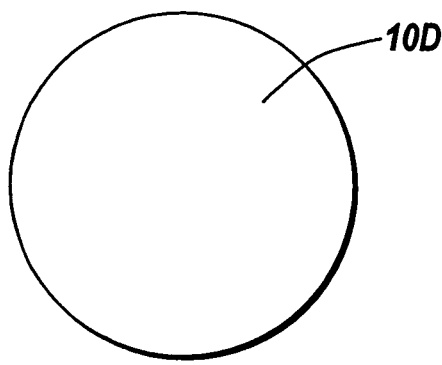
FIGS. 3A, 3B, 3C, 3D, 3E, and 3F are diagrammatic views of the cross-linked gel in accordance with another aspect of the present invention.
Figure 3B:
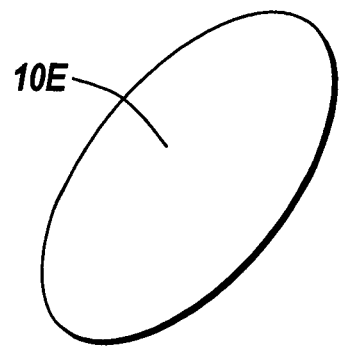
Figure 3C:
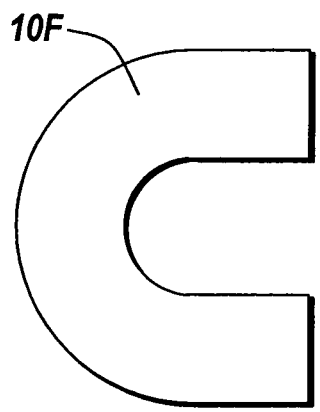
Figure 3D:
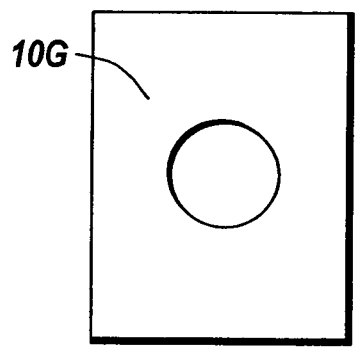
Figure 3E:
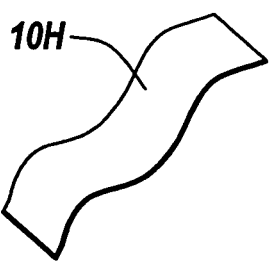
Figure 3F:
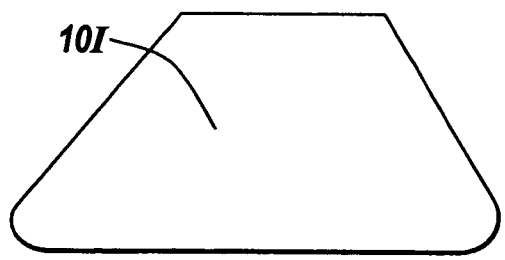

FIGS. 2A, 2B, and 2C illustrate side views of multiple different embodiments of the cross-linked gel 10 when cured. In FIG. 2A, a cross-linked gel 10A is shown having two tiers, a first tier 20 and a second tier 22. The first tier 20 and the second tier 22 as shown are formed of different materials. The different materials can be different forms of fish oil, different naturally occurring oils other than fish oil, or therapeutic components as will be discussed later herein. The different materials bind together to form the cross-linked gel 10A.

FIG. 2B shows a cross-linked gel 10B having a first tier 24, a second tier 26, and a third tier 28. In the embodiment shown, each of the tiers 24, 26, and 28 is formed of the same material. The plurality of tiers indicates the ability to create a thicker cross-linked gel 10 if desired. The greater the number of tiers, the thicker the resulting gel. The thickness of the cross-linked gel 10 can have an effect on the overall strength and durability of the cross-linked gel 10. A thicker gel is generally stronger and more durable. In addition, the thickness of the cross-linked gel 10 can also affect the duration of time that the cross-linked gel 10 lasts after implantation. A thicker cross-linked gel 10 provides more material to be absorbed by the body, and thus will last longer than a thinner cross-linked gel 10. One of ordinary skill in the art will appreciate that the thickness of the cross-linked gel 10 can vary both by varying the thickness of each tier 24, 26, and 28, and by varying the number of tiers 24, 26, and 28. Accordingly, the present invention is not limited to the particular layer combinations illustrated.

FIG. 2C shows another cross-linked gel 10C, having four tiers, a first tier 30, a second tier 32, a third tier 34, and a fourth tier 36. In this example embodiment, the first tier 30 and the third tier 34 are formed of the same material, while the second tier 32 and the fourth tier 36 are formed of a material different from each other and different form that of the first tier 30 and the third tier 34. Accordingly, this embodiment illustrates the ability to change the number of tiers, as well as the material used to form each of the tiers 30, 32, 34, and 36. Again, the different materials can be derived from different forms of fish oil, different naturally occurring oils other than fish oil, or therapeutic components as will be discussed later herein.

FIGS. 3A through 3F show additional embodiments or configurations of the cross-linked gel 10. The embodiments include cross-linked gel 10D in a circular configuration, cross-linked gel 10E in an oval configuration, cross-linked gel 10F in a U-bend configuration, cross-linked gel 10G in a square configuration having a circular aperture, cross-linked gel 10H in a wave configuration, and cross-linked gel 10I in an irregular shape configuration. Each of the configurations of the cross-linked gel 10D through 10I represent different types of configurations. The configurations illustrated are by no means the only possible configurations for the cross-linked gel 10. One of ordinary skill in the art will appreciate that the specific shape or configuration of the cross-linked gel 10 can vary as desired. A more prevalent configuration is the rectangular or oblong configuration of FIG. 1. However, FIGS. 3A through 3F illustrate a number of different alternative embodiments, and indicate some of the many possible configurations.

Figure 4:
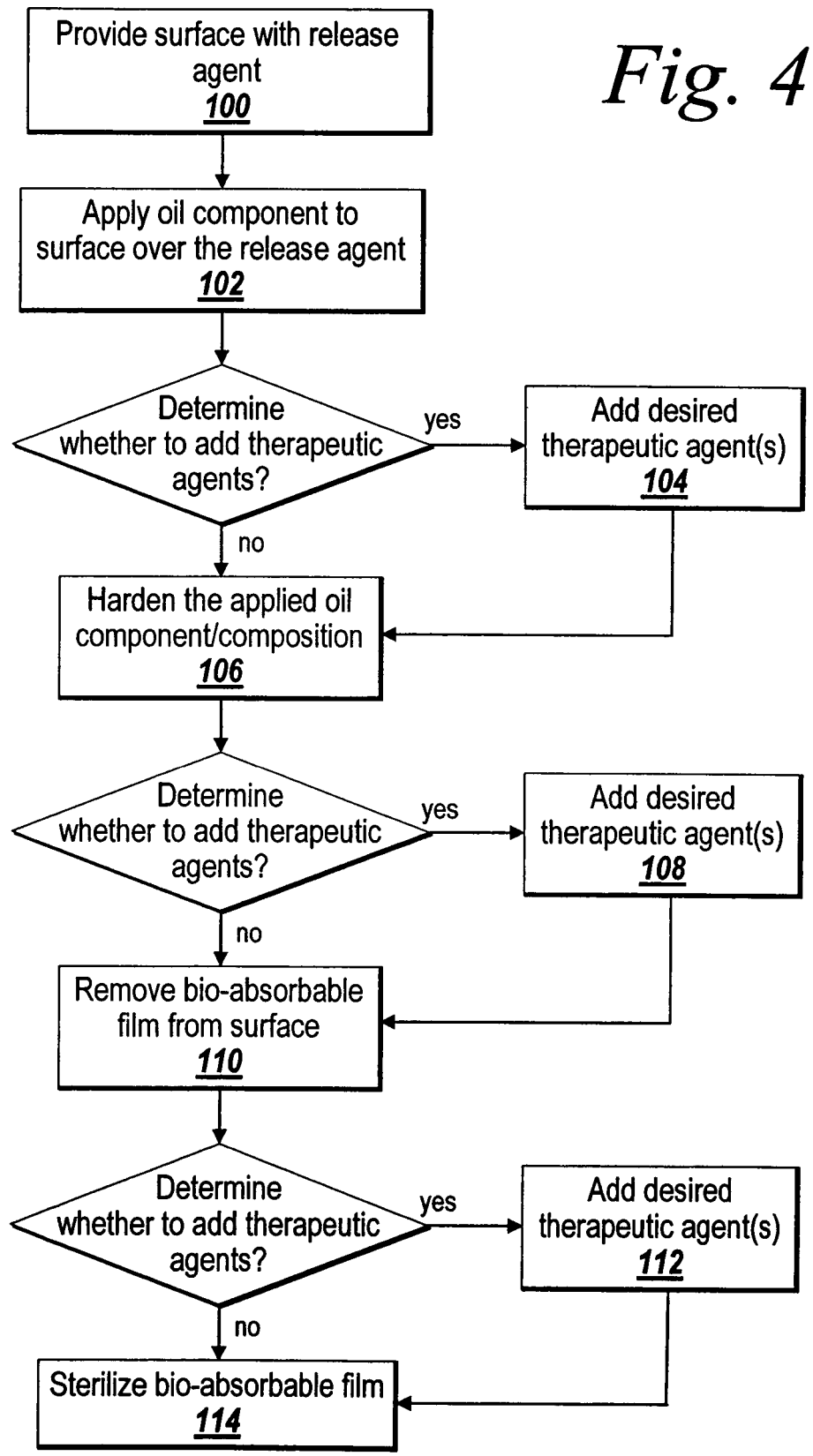
FIG. 4 is a flow chart illustrating a method of making the cross-linked gel of the present invention, in accordance with one embodiment of the present invention.

FIG. 4 is a flowchart illustrating one example method for the formation of the cross-linked gel 10. A surface is provided having a release agent (step 100). The surface can be prepared by the application of the release agent, or the release agent can be pre-existing. The release agent can be a number of different solutions, including for example, polyvinyl alcohol (PVA). The release agent can be applied in a number of different ways as well, including but not limited to spraying, dipping, coating, painting, and the like. It should be noted that the release agent can be applied to the surface immediately prior to the remaining steps or well in advance of the remaining steps, so long as when the remaining steps are executed there is a release agent on the surface.

An oil component is applied to the surface on top of the release agent (step 102). As noted previously, the oil component can be a naturally occurring oil, such as fish oil, cod liver oil, cranberry oil, or other oils having desired characteristics. In addition, the oil component can be an oil composition, meaning a composition containing oil in addition to other substances. For example, the oil composition can be formed of the oil component in addition to a solvent and/or a preservative. Solvents can include a number of different alternatives, including ethanol or N-Methyl-2-Pyrrolidone (NMP). The preservative can also include a number of different alternatives, including vitamin E compounds. One of ordinary skill in the art will appreciate that there are a number of different solvents and preservatives available for use with the oil component to form the oil composition, and as such the present invention is not limited to only those listed in the examples herein. The solvent can be useful to alter the physical properties of the oil, as well as prepare the oil for combination with a therapeutic agent as described below. The preservative can also be useful in altering the physical properties of the oil component, as well as protecting some of the beneficial properties of the oil component during certain curing processes. Such beneficial properties include the healing and anti-inflammatory characteristics previously mentioned.

The oil component can be combined with one or more therapeutic agents to form an oil composition. Thus, if the added therapeutic benefit of a particular therapeutic agent or agents is desired, the therapeutic agent(s) can be added to the oil component prior to application to the surface, along with the oil component during application to the surface (including mixing with the oil component prior to application), or after the oil component has been applied (step 104). The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure. One of ordinary skill in the art will appreciate that a number of different factors, such as those listed above in addition to others, can influence when in the process the therapeutic agent is added to the oil component, or the cross-linked gel 10. Accordingly, the present invention is not limited to the specific combinations described, but is intended to anticipate all such possible variations for adding the therapeutic agent(s).

For example, if 80% of a therapeutic agent is rendered ineffective during curing, the remaining 20% of therapeutic agent, combined with and delivered by the barrier can be efficacious in treating a medical disorder, and in some cases have a relatively greater therapeutic effect than the same quantity of agent delivered with a polymeric or other type of coating or barrier. This result can be modified with the variance of alpha-tocopherol to protect the therapeutic agent during the curing process, and then slow and extend the delivery of the therapeutic agent during absorption of the barrier layer into the tissue.

The oil component (or composition if mixed with other substances) is then hardened into the cross-linked gel 10 (step 106). The step of hardening can include hardening, or curing, such as by introduction of UV light, heat, oxygen or other reactive gases, chemical curing, or other curing or hardening method. The purpose of the hardening or curing is to transform the more liquid consistency of the oil component or oil composition into a more solid film or gel, while still maintaining sufficient flexibility to allow bending and wrapping of the film or gel as desired. However, the hardening process as described herein does not refer to or include the process of hydrogenation.

After the cross-linked gel 10 has formed, another determination is made as to whether therapeutic agents should be applied to the gel. If desired, the therapeutic agent(s) is added to the cross-linked gel 10 (step 108). Subsequently, the cross-linked gel 10 is removed from the surface (step 110). Once again, there is opportunity to apply a therapeutic agent(s) to the cross-linked gel 10 on one or both sides of the cross-linked gel 10. If such therapeutic agent(s) is desired, the therapeutic agent(s) is applied (step 112). The additional therapeutic agent can also be applied in the form of a non-cured or minimally cured oil, such as fish oil. The oil can likewise include other therapeutic agents mixed therewith. The resulting structure of such an application forms the underlying cross-linked gel 10 that is cured to form the gel, with a top coating of oil and potentially additional therapeutic agent layered on top. This structure enables the provision of a short term release of therapeutic from the oil top layer combined with a longer term release from the cured gel, which takes more time to degrade.

After application of the therapeutic agent(s), or after the cross-linked gel 10 is removed from the surface, the cross-linked gel 10 is sterilized. The sterilization process can be implemented in a number of different ways. For example, sterilization can be implemented utilizing ethylene oxide, gamma radiation, E beam, gas plasma, or vaporized hydrogen peroxide (VHP). One of ordinary skill in the art will appreciate that other sterilization processes can also be applied, and that those listed herein are merely examples of sterilization processes that result in a sterilization of the cross-linked gel 10, preferably without having a detrimental effect on the cross-linked gel.

It should be noted that the oil component or oil composition can be added multiple times to create multiple tiers in forming the cross-linked gel 10. For example, if a thicker cross-linked gel 10 is desired, additional tiers of the oil component or oil composition can be added after steps 100, 104, 106, 108, 110, or 112. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Figure 5A:
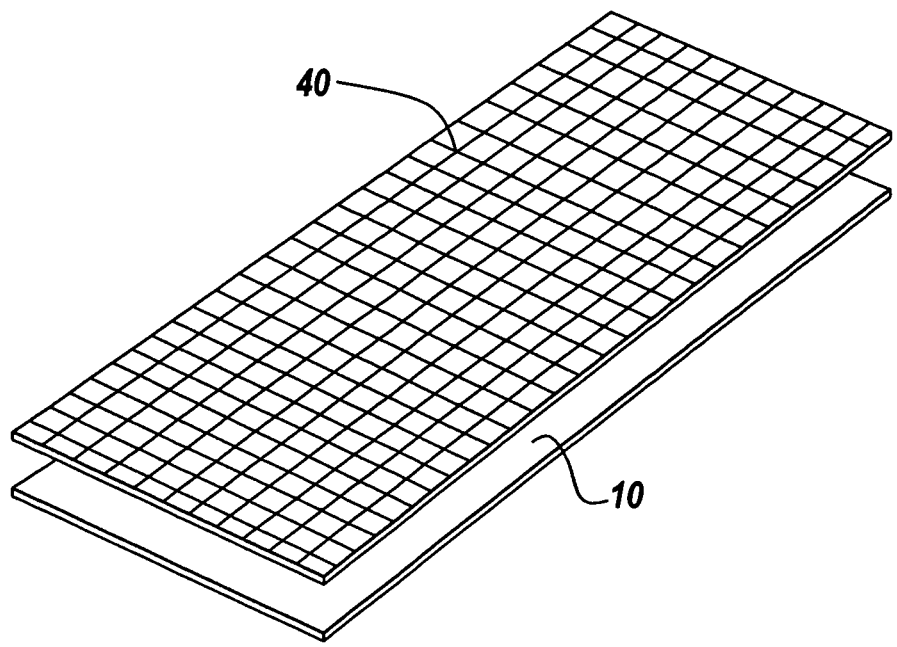
FIGS. 5A and 5B are perspective and cross-sectional views of the cross-linked gel in combination with a medical device, in accordance with one embodiment of the present invention.
Figure 5B:
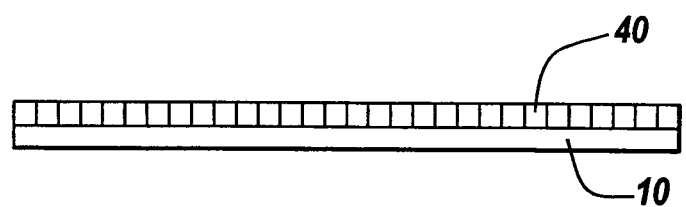

FIGS. 5A and 5B illustrate the cross-linked gel 10 and a medical device in the form of a mesh 40. In FIG. 5A, the cross-linked gel 10 and mesh 40 are shown in exploded view, while FIG. 5B shows the cross-linked gel 10 coupled with the mesh 40. The mesh 40 is merely one example medical device that can be coupled with the cross-linked gel 10. In the instance of the mesh 40, it can be useful to have one side of the mesh support a rougher surface to encourage tissue in-growth, and the other side of the mesh with an anti-adhesion, non-inflammatory, and/or anti-inflammatory surface to prevent the mesh from injuring surrounding tissue or causing inflammation. The coupling of the cross-linked gel 10 with the mesh 40 achieves such a device.

As understood by one of ordinary skill in the art, the properties of the mesh 40 and the cross-linked gel 10 can vary. There may be a requirement for the mesh 40 to have one side, or a portion of a side, that has anti-adhesion properties for a period of several days. Alternatively, multiple sides of the mesh 40 may be required to have anti-adhesion properties. As such, the cross-linked gel 10 can be applied to all sides, or portions of sides, or portions of one side of the mesh 40.

In addition, the requirement may be for the anti-adhesion properties to last several weeks, or even longer. Accordingly, the rate of degradation can also be varied by changing such properties as amount of cross-linking, thickness, and existence of additives, such as vitamin E compounds to achieve longer or shorter term anti-adhesion properties. In addition, there may be a desire to include a therapeutic agent to reduce inflammation, provide antibiotic therapy, or other therapeutic measures, in combination with the use of the mesh 40. Accordingly, the therapeutic agent(s) can be added to the cross-linked gel 10 to achieve the desired controlled release of the therapeutic agent after implantation. As previously described, combinations of cured oils top coated with lesser cured or non-cured oils and therapeutic agents can form the cross-linked gel 10.

The particular properties or characteristics of the mesh 40 are determined based on the desired use of the mesh 40. A common implementation is for the mesh 40 to be formed of a bio-compatible material, such as polypropylene, however other bio-compatible materials can be utilized, such as a mesh formed of the same or similar substance as the cross-linked gel 10 (i.e., oil based).

Figure 6:
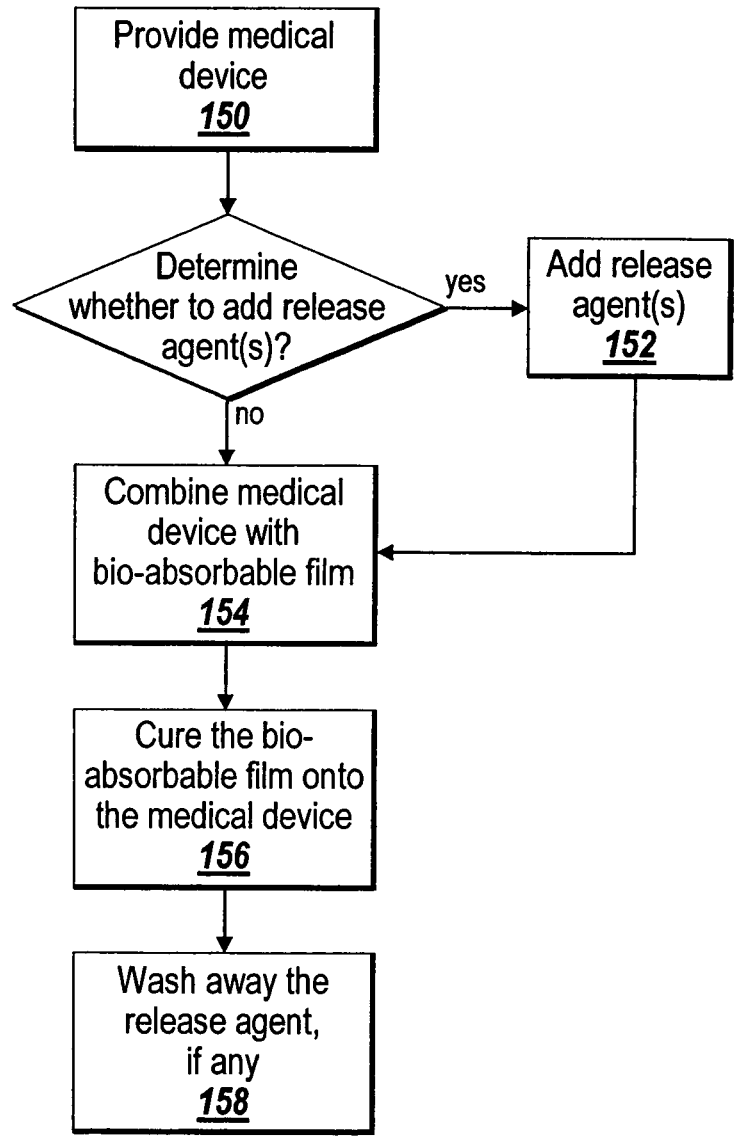
FIG. 6 is a flow chart illustrating a method of combining the cross-linked gel with a medical device, in accordance with one embodiment of the present invention.
Figure 8A:
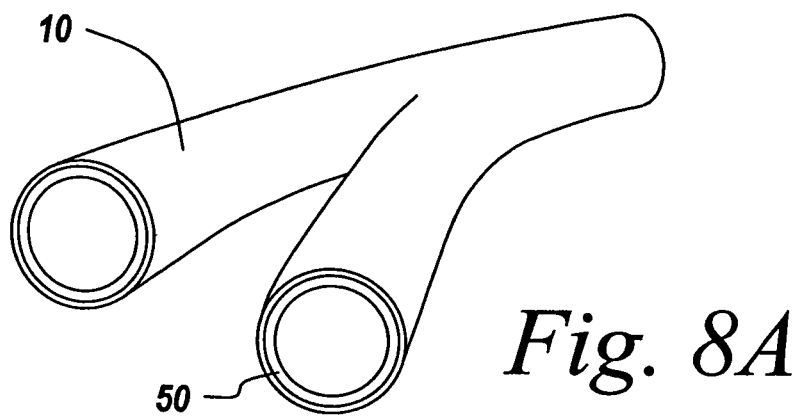
FIGS. 8A, 8B, and 8C are diagrammatic illustrations of the barrier coupled with various medical devices.
Figure 8B:
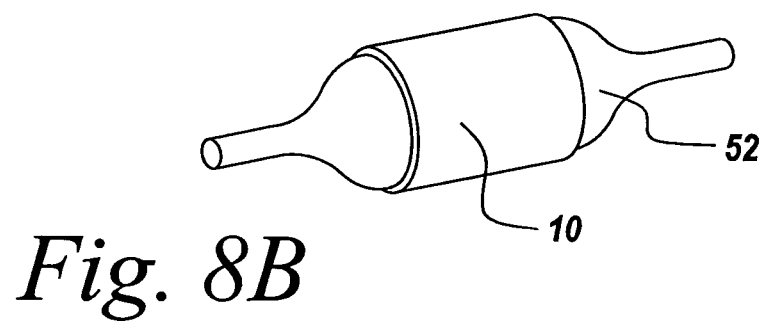
Figure 8C:
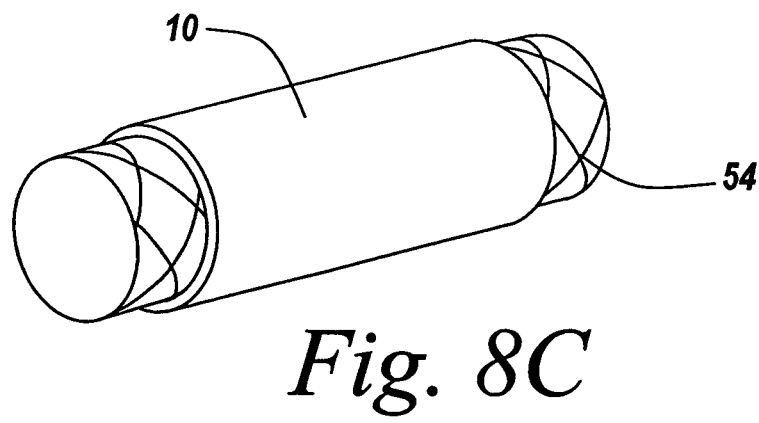

FIG. 6 is a flowchart illustrating one example method for forming the mesh 40 and cross-linked gel 10 combination. The medical device is provided (step 150). The medical device can be, for example, the mesh 40, or a graft 50, a catheter balloon 52, a stent 54, as shown in FIGS. 8A through 8C, or another form of medical device as would be understood by one of ordinary skill in the art.

A determination is made as to whether a release agent should be added to the medical device to aid in removing the device from its location (e.g., on a surface) after combination with the cross-linked gel 10. If a release agent is required, the release agent is applied to the medical device (step 152). An example release agent for such an application is polyvinyl alcohol.

The medical device is then combined with the cross-linked gel 10 (step 154). Depending on the particular medical device, the combination with the cross-linked gel 10 can be implemented more efficiently by either applying the cross-linked gel 10 to the medical device, or placing the medical device on the cross-linked gel 10. For example, in the case of the mesh 40, the mesh 40 can be placed on top of the cross-linked gel 10, or the cross-linked gel 10 can be placed on top of the mesh 40.

The medical device and the cross-linked gel are then cured to create a bond (step 156). The curing process can be one of several known processes, including but not limited to applying heat, or UV light, or chemical curing, to cure the cross-linked gel. After curing, if there is any release agent present, the release agent is washed away using water, or some other washing agent (step 158).

Figure 7:
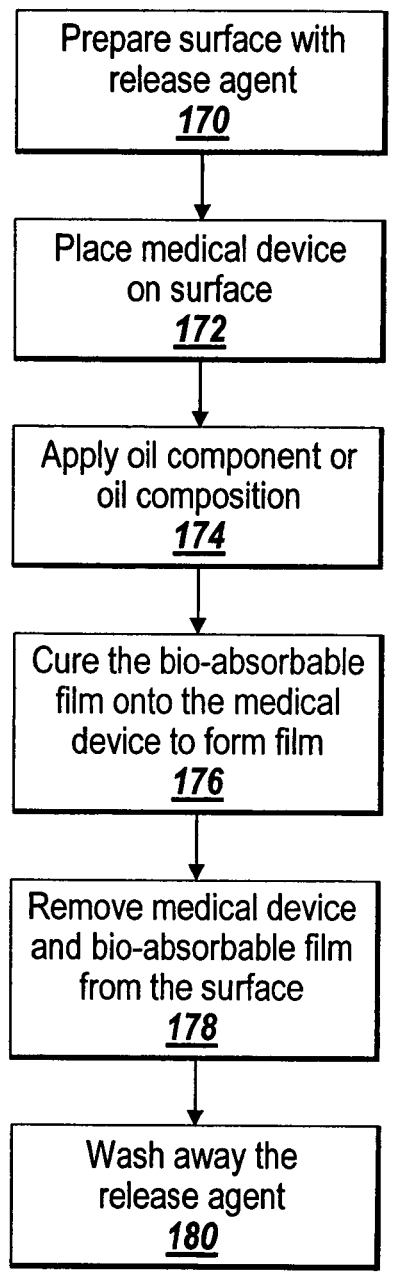
FIG. 7 is a flow chart illustrating another variation of the method of FIG. 6, in accordance with one embodiment of the present invention.

FIG. 7 is a flowchart illustrating another example method of forming a medical device with a cross-linked gel. A surface is prepared with a release agent, such as PVA (step 170). The medical device is placed on the surface (step 172). The oil component or oil composition is applied to the medical device (step 174). The oil component or oil composition can be, for example, poured or sprayed onto the medical device. The combined oil component/composition and medical device are then cured (step 176) using methods such as application of heat, UV light, oxygen, chemical cross-linker, or hardening processes, to form the cross-linked gel in combination with the medical device. The combined cross-linked gel and mesh are then removed from the surface (step 178) and the release agent is washed away (step 180).

As with the method of FIG. 6, if desired, a therapeutic agent can be added to the oil component or oil composition at any point along the process forming the combined cross-linked gel 10 and medical device, including being a component of the oil composition. As discussed previously, consideration must be given as to whether the therapeutic agent may be affected by the curing process, or other aspects of the process.

Furthermore, the formation of the oil composition can be done in accordance with different alternatives to the methods described. For example, prior to forming the cross-linked gel 10, a preservative, such as Vitamin E compounds can be mixed with the naturally occurring oil component to form the oil composition. A solvent can be mixed with a therapeutic agent, and then added to the naturally occurring oil to form the oil composition. The solvent can be chosen from a number of different alternatives, including ethanol or N-Methyl-2-Pyrrolidone (NMP). The solvent can later be removed with vacuum or heat. Other solvent alternatives can include, but are not limited to, a solvent or mixture of solvents including solvents that are generally acceptable for pharmaceutical use. Suitable solvents include, for example: alcohols and polyols, such as $C_2$-$C_6$ alkanols, 2-ethoxyethanol, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, and polypropylene glycol; amides, such as 2-pyrrolidone, 2-piperidone, 2-caprolactam, N-alkylpyrrolidone, N-methyl-2-pyrrolidone, N-hydroxyalkylpyrrolidone, N-alkylpiperidone, N-alkylcaprolactam, dimethylacetamide; esters, such as ethyl acetate, methyl acetate, butyl acetate, ethylene glycol diethyl ether, ethylene glycol dimethyl ether, propylene glycol dimethyl ether, ethyl proprionate, tributylcitrate, acetyl triethylcitrate, acetyl tributyl citrate, triethylcitrate, ethyl oleate, ethyl caprylate, ethyl cutyrate, tracetin, ϵ-caprolactone and isomers thereof, δ-valerolactorne and isomers thereof, β-butyrolactone and isomers thereof; and other solvents, such as water, dimethylsulfoxide, benzyl benzoate, ethyl lactate, acetone, methylethyl ketone, dimethylsolfone, tetrahydrofuran, decylmethylsufoxide, N,N-diethyl-m-toulamide or 1-dodecylazacycloheptan-2-one, hexane, chloroform, dichloromethane.

In addition, it should again be noted that the oil component or oil composition can be added multiple times to create multiple tiers in forming the cross-linked gel 10. If a thicker cross-linked gel 10 is desired, additional tiers of the oil component or oil composition can be added after steps 174 and 176. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Depending on the type of therapeutic agent component, the resulting cross-linked gel 10 can maintain its bio-absorbable characteristics if the therapeutic agent component is also bio-absorbable.

The therapeutic agent component, as described herein, has some form of therapeutic or biological effect. The oil component or oil composition component can also have a therapeutic or biological effect. Specifically, the cross-linked gel 10 (and its oil constituents) enable the cells of body tissue of a patient to absorb the cross-linked gel 10 itself, rather than breaking down the gel and disbursing by-products of the gel for ultimate elimination by the patient's body.

As previously stated, and in accordance with embodiments of the present invention, the cross-linked gel 10 is formed of a naturally occurring oil, or composition including a naturally occurring oil, such as fish oil, cod liver oil, cranberry oil, and the like. A characteristic of the naturally occurring oil is that the oil includes lipids, which contributes to the lipophilic action described later herein, that is helpful in the delivery of therapeutic agents to the cells of the body tissue. In addition, the naturally occurring oil can include the essential omega-3 fatty acids in accordance with several embodiments of the present invention.

It should also be noted that the present description makes use of the mesh 40 as an example of a medical device that can be combined with the cross-linked gel 10 of the present invention. However, the present invention is not limited to use with the mesh 40. Instead, any number of other implantable medical devices can be combined with the cross-linked gel 10 in accordance with the teachings of the present invention. Such medical devices include catheters, grafts, balloons, prostheses, stents, other medical device implants, and the like. Furthermore, implantation refers to both temporarily implantable medical devices, as well as permanently implantable medical devices.

FIGS. 8A, 8B, and 8C illustrate some of the other forms of medical devices mentioned above in combination with the cross-linked gel 10 of the present invention. FIG. 8A shows a graft 50 with the cross-linked gel 10 coupled or adhered thereto. FIG. 8B shows a catheter balloon 52 with the cross-linked gel 10 coupled or adhered thereto. FIG. 8C shows a stent 54 with the cross-linked gel 10 coupled or adhered thereto. Each of the medical devices illustrated, in addition to others not specifically illustrated or discussed, can be combined with the cross-linked gel 10 using the methods described herein, or variations thereof. Accordingly, the present invention is not limited to the example embodiments illustrated. Rather the embodiments illustrated are merely example implementations of the present invention.

Returning to the step of curing as described herein, the step can have a number of different variations and permutations that ultimately influence the properties of the resulting cured cross-linked gel, and any therapeutic agents if include therein. In this instance making use of a naturally occurring oil, such as fish oil, such oils or oil compositions as described herein can be heated to increase viscosity. The level of UV light and the time duration of exposure of the oil or oil composition will affect how viscous the oil or oil composition becomes.

In addition, combining pre-cured, highly viscous oil with untreated oil results in a faster cure time of the resulting combination when forming the cross-linked gel. Also, taking a pre-cured oil and decreasing its viscosity slightly with solvent will result in a faster cure time as well. To demonstrate the effectiveness of a combination of UV and heat from UV curing relative to exclusive heat curing, the following example is provided.

EXAMPLE #1

UV light was utilized to initiate curing in fish oil. No sensitizer was added to the fish oil during UV curing. In addition, the UV lamps used were of relatively low power (15W at 252 nm) and reached a temperature of 88-90° F. during curing. Thus, the films cured using the UV process described here were cured using a combination of photo-oxygenation and autoxidation initiation pathways. Also, since no sensitizer was added directly to the fish oil to create the singlet oxygen needed to cure the fish oil, the kinetics of the process are similar, but at a lower efficiency.

An FTIR spectrum analysis for heat and UV-heat cured fish oil coatings encapsulating polypropylene mesh was performed. The heat cured mesh coating was created by heating the coating at 200° F. for 48 hours in a high airflow oven. The UV-heat cured mesh coating was created by curing for 29 hours with the "rough side" of the mesh facing up toward the UV lamp (15 W at 252 nm, temperature of chamber 88-90° F.), followed by flipping the mesh over for an additional 19 hours, with a total curing time of 48 hours. There was no high airflow used in the UV-air curing experiment.

The resulting cured coatings had several differences. The trans C=C bonds were almost completely consumed using the UV-heat curing method; whereas they were still present using heat curing alone. In addition, the UV-heat curing spectrum possess more OH bands (indicative of alcohol and fatty acid byproduct formation), less CH2 band intensity, greater anhydride/aliphatic peroxide/lactone cross-linking, and more fatty acid/ketone C=O absorption, relative to the purely heat cured coating. Also, similar to the heat cured fish oil coating, a majority of the ester bonds of the fish oil triglyceride headgroup are retained using the UV-heat curing method.

The coating of the UV-heat curing method contains a greater amount of oxidized byproducts than the coating of the heat cured method, as evidenced by greater OH (alcohol and fatty acid) and fatty acid/ketone C=O bands. In addition, due to the increase in hydroperoxide formation due to photo-oxygenation chemistry, there is a greater amount of anhydride/aliphatic peroxide/lactone cross-linking absorption. Furthermore, there are a greater amount of carbon-carbon cross-linking, and the UV-heat cured mesh coating contains shorter hydrocarbon chain lengths than the heat cured method.

As evidenced by the examples herein, by using UV light in addition to heat, the fish oil curing chemistry can differ in the resulting coatings prepared over a similar time frame. Specifically, the UV-heat cured coating possesses greater amounts of oxidized byproducts, greater amounts of cross-linking, and shorter hydrocarbon chain segments. Ultimately, the resulting coating having been cured by UV-heat degrades in a manner that releases drugs contained therein in a similar but different manner to the heat cured coatings. The below examples illustrate this relationship.

EXAMPLE #2

UV-Cured: Cyclosporine a Drug Delivery on Encapsulated Mesh

Figure 10:
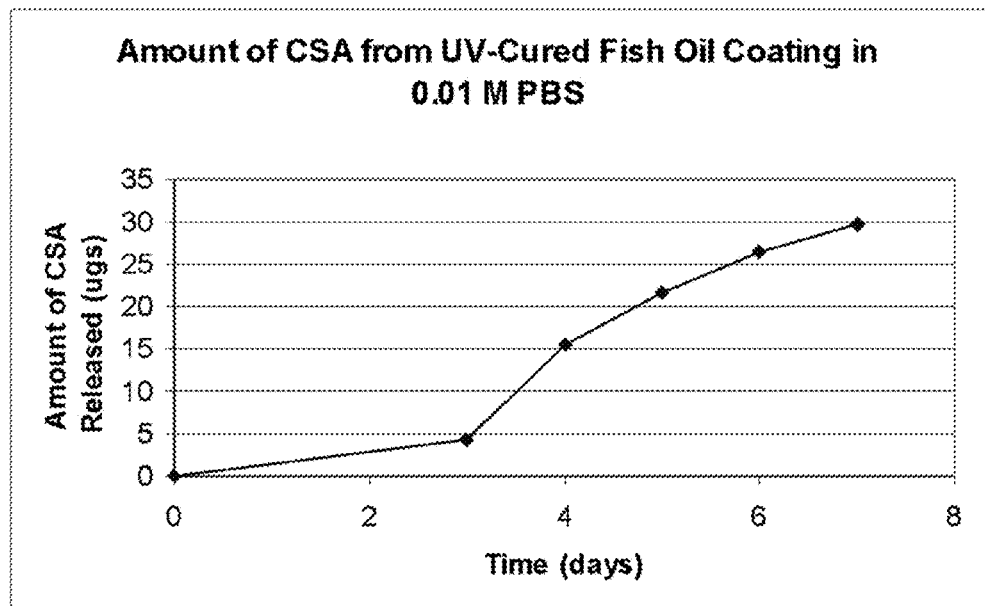
FIG. 10 is a graph showing a release rate of a cured coating according to an example embodiment disclosed herein.

A fish oil and CSA encapsulated mesh was manufactured using UV lamps (15 watts, at 88-90° F.) for 48 hours, using 125 ul of formulation per 1×1" sample. Some "pin holes" were observed in the coating. The formulation was 2.85% CSA in Fish Oil with no solvent, but with heating at 37° C. for 1 hour with vortexing. An average amount extracted after curing (as measured by HPLC) was 265 micrograms. Based on coating weight, this represents an 8% CSA survival rate. The graph of FIG. 10 shows the dissolution rate of the cured coating.

EXAMPLE #3

Figure 11:
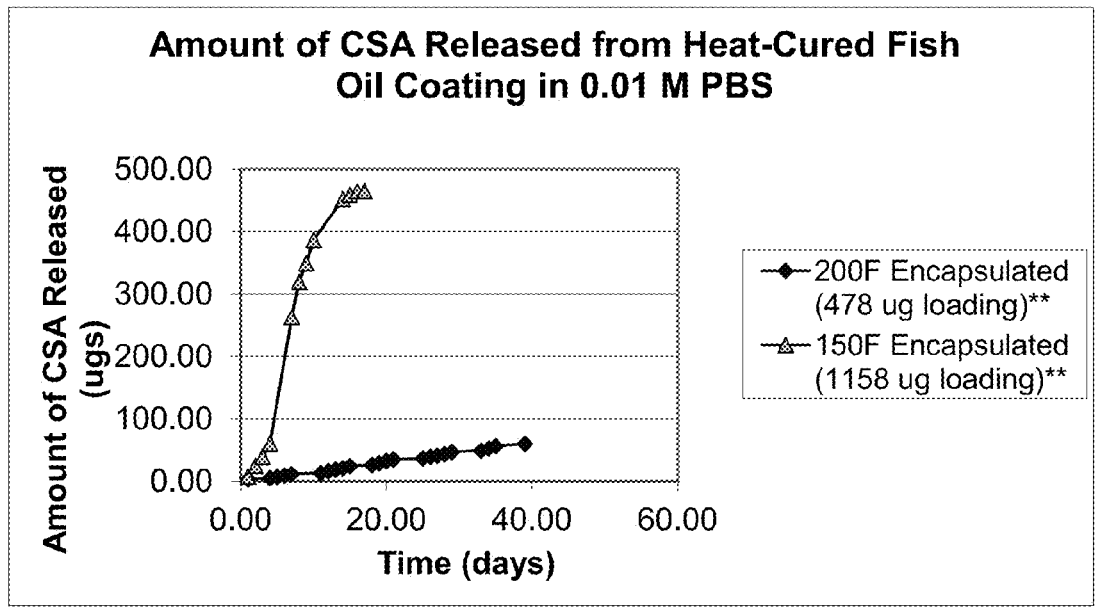
FIG. 11 is a graph showing a drug release rate of cured coatings according to an example embodiment disclosed herein.

Heat-Cured: Comparison of Cyclosporine A—Pure Fish Oil Encapsulated Mesh Coatings Using 200° F. and 150° F. Curing A coated mesh was manufactured with a formulation of 2.84% Cyclosporine in Fish Oil. No solvent was used, and Cyclosporine was soluble in the fish oil with slight heating at 37° C. One coating was heated for 3 days at 150° F. and a second coating was heated for 24 hours at 200° F. After curing, drug loading was about 478 ug (14.22% recovery) for the 200° F. cured mesh and about 1158 ug (26.00% recovery) for the 150° F. cured mesh. The coatings were then degraded and the drug release measured as illustrated in the graph of FIG. 11. It is noted that the amount recovered is dependent on the coating weight and amount of drug detected using HPLC methods after drug extraction from the cured fish oil coating.

Figure 12:
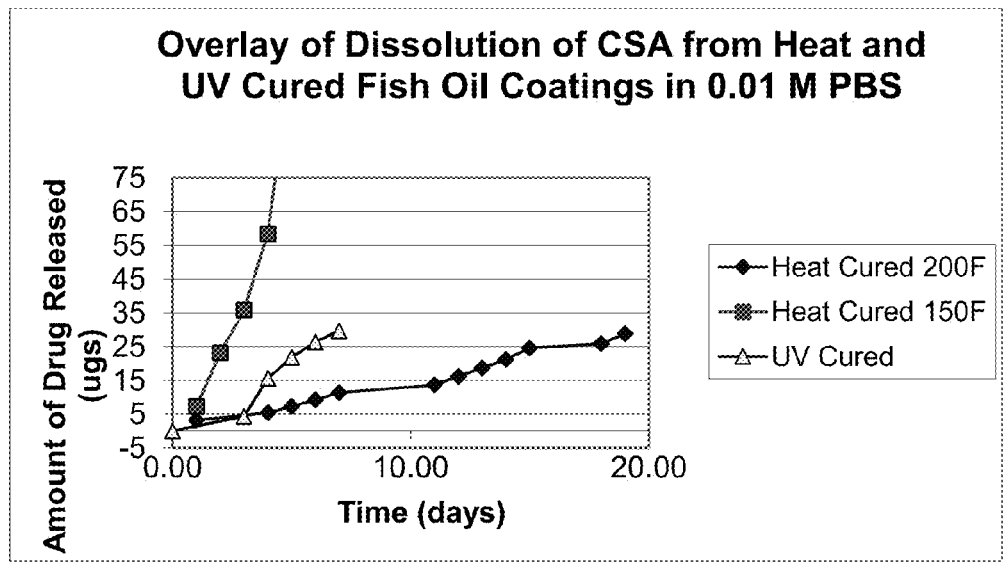
FIG. 12 is a graph comparing the results illustrated in FIGS. 10 and 11.

Based on the measured results of the above two examples of curing, the first being two variations of heat curing and the second being a variation of UV curing, the graph of FIG. 12 compares the degradation of the coatings.

The graph of FIG. 12 illustrates that the 150° F. cured coating, which has less cross-linking, results in a faster drug release than the 200° F. cured coating, which possess more cross-linking. This example demonstrates the ability to load an anti-proliferative, Cyclosporine A, into cured fish oil encapsulated mesh coatings and by using temperature to control the cross-linking properties of that coating, the drug dissolution release profile is significantly altered. The UV-cured coating shows a dissolution profile that is more rapid that the 200° F. cured mesh, but slower than the 150° F. cured mesh.

EXAMPLE #4

UV-Cured Rapamycin Drug Delivery on Encapsulated Mesh

Figure 13:
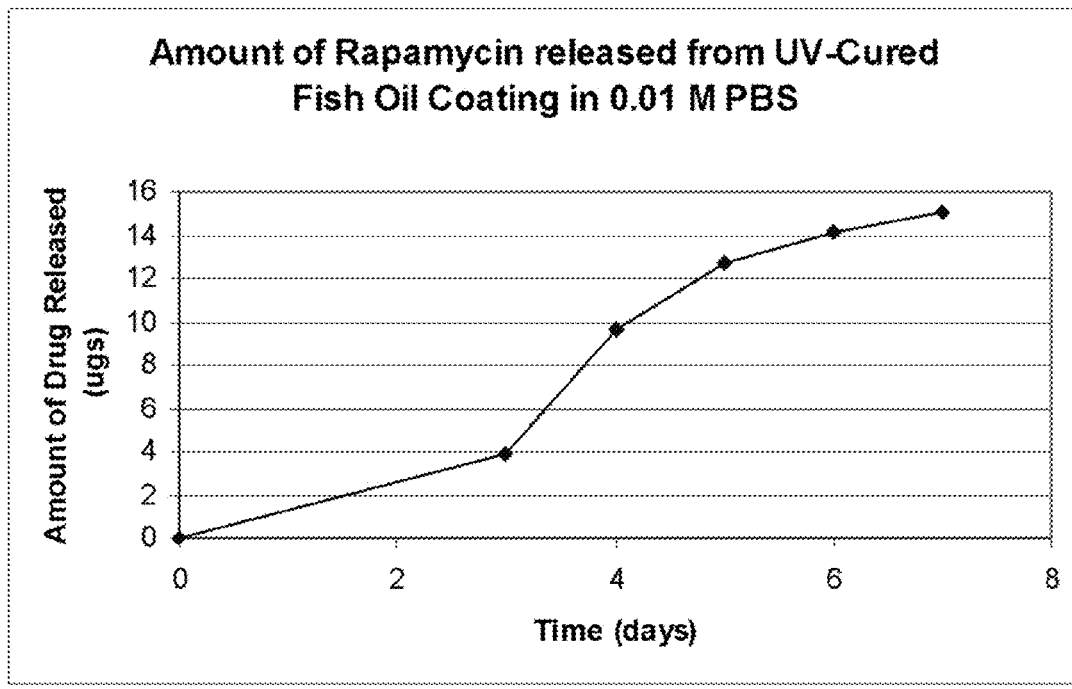
FIG. 13 is a graph showing a drug release rate of a cured coating according to an example embodiment disclosed herein.

A coated mesh (mesh structure encapsulated in the coating) was manufactured and cured using UV lamps (15 watts, at 88-90° F.) for 48 hours. An amount of 125 ul of formulation was used per 1×1" sample. Some "pin holes" were observed in the coating. The formulation was about 4.58% Rapamycin in Fish Oil (where the percentage was based on no remaining nMP in formulation, where any trace amounts should be removed after curing). An average amount of drug was extracted based on HPLC analysis in the amount of about 611 micrograms. Based on coating weight, this represents an 18% Rapamycin survival rate. The degradation and drug release is depicted in the graph of FIG. 13.

EXAMPLE #5

Figure 14:
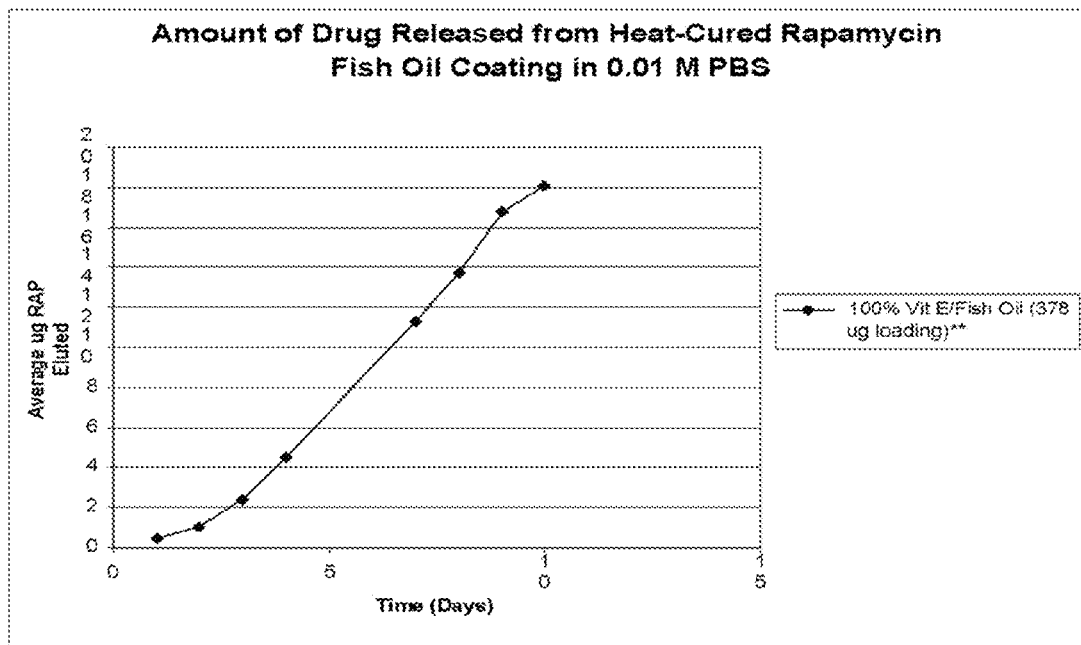
FIG. 14 is a graph showing a drug release rate of a cured coating according to an example embodiment disclosed herein.

Heat Cured Rapamycin Drug Delivery in Encapsulated Fish Oil Mesh Using 150° F. Curing Conditions A formulation of about 4.88% Rapamycin (after solvent removal) in fish oil was provided in the coating. The coating was cured by heating for 3 days at 150° F. Initial drug loading measured after curing using HPLC was about 378 ug. The coating was degraded and drug release measured as depicted in the graph of FIG. 14. It is noted that the amount recovered is dependent on the coating weight and amount of drug detected using HPLC methods after drug extraction from the cured fish oil coating.

Figure 15:
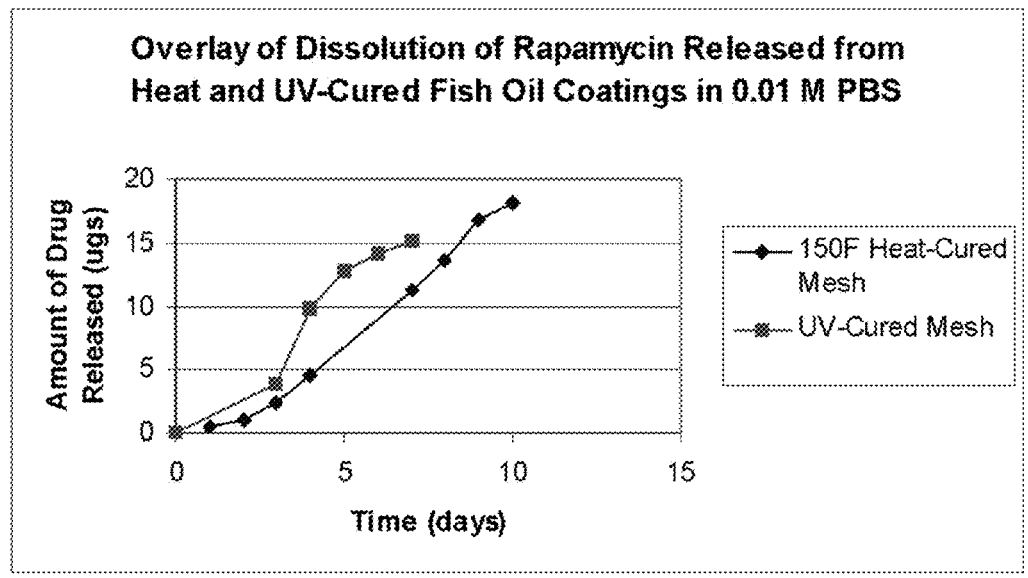
FIG. 15 is a graph showing a comparison of the results illustrated in FIGS. 13 and 14.

Based on the measured results of the above two examples of curing, the first being two UV-heat curing and the second being a variation of heat curing, the graph of FIG. 15 compares the degradation of the coatings.

These results demonstrate that UV-cured fish oil coatings may result in a faster dissolution than 150° F. heat-cured coatings when loading Rapamycin in the coating.

In view of the above examples, the previously described methods of manufacture that include a curing step can be implemented using a UV-heat curing approach. In accordance with the method of the present invention, the curing process (such as referred to in step 156 in FIG. 6 and step 176 in FIG. 7 of the present description) can be modified to result in different cross-linked gels. The process can be implemented using heat, as previously described, or can be implemented using UV-heat. Given the rate of degradation of the UV-heat cured coating, if a desired rate of coating degradation approximates the rates achievable by UV-heat curing, then UV-heat curing can be utilized. In addition, if a greater amount of oxidized byproducts, greater amounts of cross-linking, and shorter hydrocarbon chain segments, then UV-heat curing can be selected over heat curing. It should be appreciated that the intensity and duration of the UV light can be varied to alter the curing process, as desired. Generally speaking, a greater intensity for a greater duration will result in more cross-linking and more complete curing of the oil or substance being cured versus a lesser intensity and a lesser duration, which will result in fewer total cross-linking.

Figure 9:
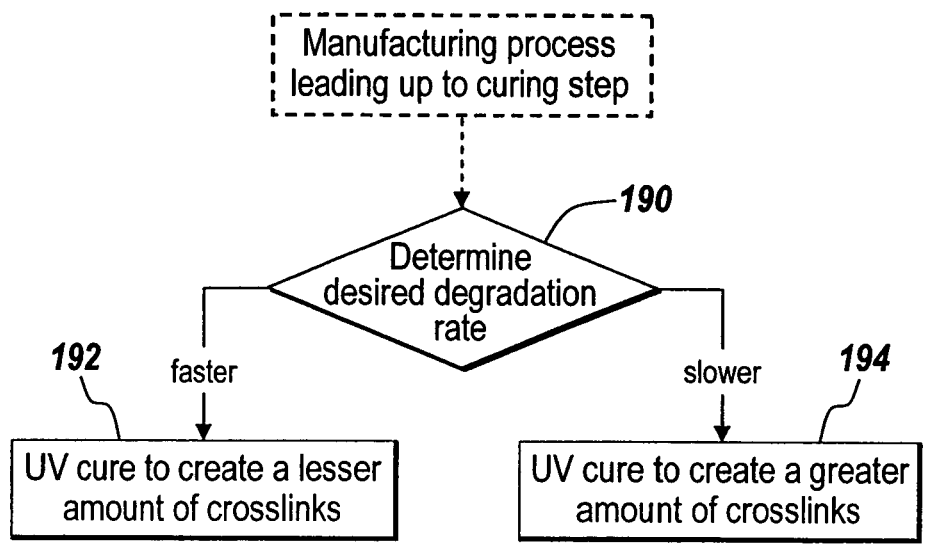
FIG. 9 is a flow chart illustrating one example method of curing to form the cross-linked gel.

FIG. 9 shows a flowchart in which considerations are made during the curing process to result in a cured or partially cured cross-linked gel that has specific desired characteristics. In accordance with the method of the present invention, the curing process (such as referred to in step 156 in FIG. 6 and step 176 in FIG. 7 of the present description) can be modified to result in different cross-linked gels. At some point in time prior to beginning the curing portion of the process, a determination is made as to whether a relatively fast but shorter term degradation (corresponding to a faster drug release rate when a drug is included) is desired, or a relatively slower but longer term degradation (corresponding to a slower drug release rate when a drug is included) is desired (step 190). If a relatively faster but shorter term drug release rate is desired, a determination is made to cure in a manner that will result in an amount of cross-links relatively lesser than otherwise possible (step 192). If a relatively slower but longer term drug release rate is desired, a determination is made to cure in a manner that will result in an amount of cross-links relatively greater than the shorter term drug release rate amount, and relatively closer to a maximum possible amount of cross-links to form the gel (step 194).

In general, a higher UV light intensity will result in a greater number of cross-links than a lower UV light intensity. Furthermore, in general, a relatively longer duration of cure time will result in a greater number of cross-links than a relatively shorter duration of cure time.

Modifying the starting pre-cured viscosity or pre-cured oil concentration in the mixture will enhance the curing speed. One of ordinary skill in the art will appreciate that the scope of the present invention is not limited to only coating on the mesh, but rather has application to other medical devices, or as a stand-alone film.

The curing conditions utilized, such as the duration of time and the intensity of UV light can influence the amount of cross-linking that occurs in the cross-linked gel (i.e., the cross-link density). Cured fish oil coatings enable regulation of the release profile of drug-loaded oil-based coatings from implantable devices. The release profile can be controlled through changes in oil coating chemistry by varying coating composition, UV light intensity, and cure times. The position of the drug-containing layer on the coated device provides an additional mechanism to alter the release profile of the drug-loaded fish oil coating. This can be achieved by either loading the drug into the encapsulating base layer of the device, or by coating a topcoat overlayer coating onto the previously cured encapsulating base layer.

More specifically, curing conditions utilized to form the cross-links, such as time and intensity can influence the amount of coating cross-linking density and byproduct formation, which in turn effects the coating degradation. Thus, by altering the curing conditions employed, the dissolution rate of the therapeutic compound of interest is also altered.

Furthermore, the oil component itself, in the form of fish oil for example, can provide therapeutic benefits in the form of reduced inflammation, and improved healing, if the fish oil composition is not substantially modified during the process that takes the naturally occurring fish oil and forms it into the cross-linked gel 10. Some prior attempts to use natural oils as coatings have involved mixing the oil with a solvent, or curing the oil in a manner that destroys the beneficial aspects of the oil. The solvent utilized in the example cross-linked gel 10 embodiment of the present invention (NMP) does not have such detrimental effects on the therapeutic properties of the fish oil. Thus the benefits of the omega-3 fatty acids, and the EPA and DHA substances are substantially preserved in the cross-linked gel of the present invention.

Therefore, the cross-linked gel 10 of the present invention includes the bio-absorbable naturally occurring oil (i.e., fish oil). The cross-linked gel 10 is thus able to be absorbed by the cells of the body tissue. With the present invention, because of the lipophilic action enabled by the bio-absorbable lipid based cross-linked gel 10 of the present invention, the intake by the tissue cells of the cross-linked gel 10, and any therapeutic agent component, is substantially controlled by the cells themselves. In configurations using polymer based materials, the drugs were released at a rate regardless of the reaction or need for the drug on the part of the cells receiving the drug. With the cross-linked gel 10 of the present invention, the cells can intake as much of the cross-linked gel 10, and correspondingly the therapeutic agent, as is needed by the damaged cell requiring treatment.

In addition, the bio-absorbable nature of the cross-linked gel 10 results in the cross-linked gel 10 being completely absorbed over time by the cells of the body tissue. There is no break down of the cross-linked gel 10 into sub parts and substances that are inflammatory and are eventually distributed throughout the body and in some instances disposed of by the body, as is the case with biodegradable synthetic polymer coatings. The bio-absorbable nature of the cross-linked gel 10 of the present invention results in the cross-linked gel 10 being absorbed, leaving only the medical device structure, if the cross-linked gel 10 is not implanted alone. There is no foreign body inflammatory response to the cross-linked gel 10.

In addition, the cross-linked gel 10 provides a lubricious or anti-adhesive surface against tissue. The cross-linked gel 10 itself can provide an anti-adhesion barrier between two sections of tissue, or the cross-linked gel 10 can form an anti-adhesion surface on a medical device, such as the mesh 40. The use of the naturally occurring oil, such as fish oil, provides extra lubrication to the surface of the medical device, which helps to reduces injury. With less injury, there is less of an inflammatory response, and less healing required. Likewise the fatty acid derived cross-linked gel that makes up the cross-linked gel maintains anti-inflammatory properties and non-inflammatory properties, which also substantially lowers the inflammatory response of the tissue. The reduced inflammation also reduces adhesions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. An ultraviolet (UV) light cured gel, the gel comprising:
fish oil, wherein the fish oil comprises unsaturated fatty acids;
wherein the fish oil is in a state of having been cured by application of UV light to cross link the unsaturated fatty acids by ester bonds in a substantially random configuration to form the gel;
wherein the gel is bioabsorbable;
wherein the gel further comprises a therapeutic agent; and
wherein the amount of curing is controlled by the application of the UV light in such a way that the gel is configured to provide controlled release of the therapeutic agent.

2. An ultraviolet (UV) light cured gel, the gel comprising:
fish oil, wherein the fish oil comprises unsaturated fatty acids;
wherein the fish oil is in a state of having been cured by application of UV light to cross link the unsaturated fatty acids by ester bonds in a substantially random configuration to form the gel;
wherein the gel is bioabsorbable;
wherein the gel further comprises a therapeutic agent; and
wherein following implantation of the gel in a patient, the gel degrades and thereby releases the therapeutic agent.

3. The gel of claim 2, wherein the fish oil comprises at least a partially cured oil or oil composition.

4. The gel of claim 2, wherein the gel is configured to release the therapeutic agent over at least about seven days following implantation.

5. The gel of claim 4, wherein the gel is formed with application of UV light at 252 nm.

6. The gel of claim 4, wherein the gel is formed with application of UV light for 48 hours.

7. The gel of claim 4, wherein the gel is formed with application of UV light at 252 nm for 48 hours.

8. The gel of claim 2, wherein the gel is configured to provide controlled release of the therapeutic agent.

9. The gel of claim 2, wherein the gel exhibits at least one property selected from the group consisting of anti-inflammatory properties, non-inflammatory properties, and wound healing properties.

10. The gel of claim 2, wherein the gel has been sterilized with a method of sterilization selected from the group of methods of sterilization consisting of ethylene oxide, gamma radiation, e-beam, steam, gas plasma, and vaporized hydrogen peroxide (VHP).

11. The gel of claim 2, wherein the gel is configured as a coating on a medical device or as a stand-alone film.

12. The gel of claim 2, wherein the fish oil is pre-treated to increase viscosity prior to curing.

13. The gel of claim 2, further comprising vitamin E.

14. An ultraviolet (UV) light cured gel, the gel comprising:
fish oil, wherein the fish oil comprises unsaturated fatty acids;
wherein the fish oil is in a state of having been cured by application of UV light to cross link the unsaturated fatty acids by ester bonds in a substantially random configuration to form the gel;
wherein the gel is bioabsorbable;
wherein the gel further comprises an anti-proliferative agent; and
wherein following placement of the gel in a 0.01M PBS solution, the gel degrades and thereby releases the anti-proliferative agent.

15. The gel of claim 2, wherein the therapeutic agent is selected from the group consisting of antioxidants, anti-inflammatory agents, anti-coagulant agents, drugs to alter lipid metabolism, anti-proliferatives, anti-neoplastics, tissue growth stimulants, functional proteins, anti-infective agents, imaging agents, anesthetic agents, chemotherapeutic agents, tissue absorption enhancers, anti-adhesion agents, germicides, analgesics, and antiseptics.

* * * * *